United States Patent [19]

Ticehurst et al.

[11] Patent Number: 5,516,630
[45] Date of Patent: May 14, 1996

[54] METHODS OF DETECTING HEPATITIS A VIRUS

[75] Inventors: John R. Ticehurst, Kensington, Md.; David Baltimore, New York, N.Y.; Stephen M. Feinstone, Washington, D.C.; Robert H. Purcell, Boyds, Md.; Vincent R. Racaniello, Scotch Plains, N.J.; Bahige M. Baroudy, Cincinnati, Ohio

[73] Assignee: The United States of America as represented by the Department of Health and Human Services, Washington, D.C.

[21] Appl. No.: 788,262

[22] Filed: Nov. 6, 1991

Related U.S. Application Data

[63] Continuation-in-part of Ser. No. 256,135, Oct. 6, 1988, abandoned, which is a continuation of Ser. No. 654,942, Sep. 27, 1984, abandoned, which is a continuation-in-part of Ser. No. 537,911, Sep. 30, 1983, abandoned.

[51] Int. Cl.$^6$ ........................................ C12Q 1/70
[52] U.S. Cl. .......................... 435/5; 536/23.1; 536/23.72
[58] Field of Search ............................... 435/5; 436/501; 935/77, 78; 536/23.1, 23.72

[56] References Cited

FOREIGN PATENT DOCUMENTS 0062286 10/1982 European Pat. Off. .
3112338 10/1982 Germany .

OTHER PUBLICATIONS

Von der Helm et al. J. Virol. Methods. 3:37–43(1981) Cloning of Hepatitis A virus genome.
Max von Helm, (2nd International. Von Pett. Symposium, pp. 63–65) (1983).

Primary Examiner—Margaret Parr
Assistant Examiner—Eggerton Campbell
Attorney, Agent, or Firm—Morgan & Finnegan

[57] ABSTRACT

Methods for producing HAV cDNA, products thereof, and uses thereof, are described. HAV cDNA is produced, for example, by reverse transcribing HAV RNA and subsequently inserting the HAV cDNA into bacterial plasmids by genetic-engineering techniques. Transformed bacteria are then cloned and cultured to produce replicated chimetic plasmids containing the HAV cDNA. Such HAV cDNA is useful in assaying for the presence of HAV and in the production of HAV antigen and in the production of antibodies against HAV.

13 Claims, 25 Drawing Sheets

FIG. 7A

```
                                                           31
TCC GGA GTC CCT CTT GGA AGT CCA TGG TGA
SER GLY VAL PRO LEU GLY SER PRO TRP END
                                                          121
TTC CCT TTC CTA TTC CCT TTG TTT TGC TTG
PHE PRO PHE LEU PHE PRO LEU PHE CYS LEU
                                                          211
TTT TCA CGC TTT CTG TCT TCT TTC TTC CAG
PHE SER ARG PHE LEU SER SER PHE PHE GLN
                                                          301
CAT GGA GCT GTA GGA GTC TAA ATT GGG GAC
HIS GLY ALA VAL GLY VAL END ILE GLY ASP
                                                          391
TCC ACA AGG GGT AGG CTA CGG GTG AAA CCT
SER THR ARG GLY ARG LEU ARG VAL LYS PRO
                                                          481
GAG TTG TTA AGA CAA AAA CCA TTC AAC GCC
GLU LEU LEU ARG GLN LYS PRO PHE ASN ALA
                                                          571
GGC TTA ATT CCA GAC CTC TCT GTG CTT AGG
GLY LEU ILE PRO ASP LEU SER VAL LEU ARG
                                                          661
GAC TGT TCT TTG GGG CCT TAT GTG GTG TTT
ASP CYS SER LEU GLY PRO TYR VAL VAL PHE
                                                          751
TCT AGA CAA GGT ATT TTC CAG ACT GTT GGG
SER ARG GLN GLY ILE PHE GLN THR VAL GLY
                                                          841
GTT GAT AGG ACT GCA GTG ACT GGT GCT TCT
VAL ASP ARG THR ALA VAL THR GLY ALA SER
```

FIG. 7B

```
                                                      61
GGG GAC TTG ATA CCT CAC CGC CGT TTG CCT
GLY ASP LEU ILE PRO HIS ARG ARG LEU PRO
                                                     151
TAA ATA TTA ATT CCT GCA GGT TCA GGG TTC
END ILE LEU ILE PRO ALA GLY SER GLY PHE
                                                     241
GGC TCT CCC CTT GCC CTA GGC TCT GGC CGT
GLY SER PRO LEU ALA LEU GLY SER GLY ARG
                                                     331
ACA GAT GTT TGG AAC GTC ACC TTG CAG TGT
THR ASP VAL TRP ASN VAL THR LEU GLN CYS
                                                     421
CTT AGG CTA ATA CTT CTA TGA AGA GAT GCC
LEU ARG LEU ILE LEU LEU END ARG ASP ALA
                                                     511
GGA GGA CTG ACT CTC ATC CAG TGG ATG CAT
GLY GLY LEU THR LEU ILE GLN TRP MET HIS
                                                     601
GCA AAC ATC ATT TGG CCT TAA ATG GGA TTC
ALA ASN ILE ILE TRP PRO END MET GLY PHE
                                                     691
GCC TCT GAG GTA CTC AGG GGC ATT TAG GTT
ALA SER GLU VAL LEU ARG GLY ILE END VAL
                                                     781
AGT GGT CTT GAC CAC ATC CTG TCT TTG GCA
SER GLY LEU ASP HIS ILE LEU SER LEU ALA
                                                     871
TAT TTT ACT TCT GTG GAT CAA TCT TCA GTT
TYR PHE THR SER VAL ASP GLN SER SER VAL
```

FIG. 7C

```
                                                                  9 1
AGG CTA TAG GCT AAA TTT TCC CTT TCC CTT
ARG LEU END ALA LYS PHE SER LEU SER LEU
                                                                 181
TTA AAT CTG TTT CTC TAT AAG AAC ACT CAT
LEU ASN LEU PHE LEU TYR LYS ASN THR HIS
                                                                 271
TGC GCC CGG CGG GGT CAA CTC CAT GAT TAG
CYS ALA ARG ARG GLY GLN LEU HIS ASP END
                                                                 361
TAA CTT GGC TTT CAT GAA TCT CTT TGA TCT
END LEU GLY PHE HIS GLU SER LEU END SER
                                                                 451
TTG GAT AGG GTA ACA GCG GCG GAT ATT GGT
LEU ASP ARG VAL THR ALA ALA ASP ILE GLY
                                                                 541
TGA GTG GAT TGA CTG TCA GGG CTG TCT TTA
END VAL ASP END LEU SER GLY LEU SER LEU
                                                                 631
TGT GAG AGG GGA TCC CTC CAT TGA CAG CTG
CYS GLU ARG GLY SER LEU HIS END GLN LEU
                                                                 721
TTT CCT CAT TCT TAA ATA ATA ATG AAC ATG
PHE PRO HIS SER END ILE ILE MET ASN MET
                                                                 811
GAC ATT GAG GAA GAG CAA ATG ATT CAA TCA
ASP ILE GLU GLU GLU GLN MET ILE GLN SER
                                                                 901
CAT ACA GCT GAG GTT GGA TCA CAC CAG GTT
HIS THR ALA GLU VAL GLY SER HIS GLN VAL
```

FIG. 7D

```
                                                    931
GAA CCT TTG AGA ACC TCT GTT GAT AAA CCC
GLU PRO LEU ARG THR SER VAL ASP LYS PRO
                                                   1021
ACA CAT GCT CTT TTC CAT GAA GTT GCA AAA
THR HIS ALA LEU PHE HIS GLU VAL ALA LYS
                                                   1111
CAT ACA TAT GCA AGA TTT GGC ATT GAA ATT
HIS THR TYR ALA ARG PHE GLY ILE GLU ILE
                                                   1201
GGT GAC CAG AGC TAT GGT TCT ATA GCA TCA
GLY ASP GLN SER TYR GLY SER ILE ALA SER
                                                   1291
GTT CCA TTT ATT TAC ACA AGA GGT GCT TAC
VAL PRO PHE ILE TYR THR ARG GLY ALA TYR
                                                   1381
AAT ATT GGG ACA GGA ACT TCA GCT TAT ACT
ASN ILE GLY TER GLY THR SER ALA TYR THR
                                                   1471
ACA CAA ATG ATG AGA AAT GAA TTT AGG GTC
THR GLN MET MET ARG ASN GLU PHE ARG VAL
                                                   1561
TTT GCT TTG GAT CAG GAA GAT TGG AAA TCT
PHE ALA LEU ASP GLN GLU ASP TRP LYS SER
                                                   1651
ACT TTG GCT GCT CAG TTT CCA TTT AAT GCT
THR LEU ALA ALA GLN PHE PRO PHE ASN ALA
                                                   1741
ACA AAT ACG AAT CCT GAC CAA AAA TGT ATA
```

FIG. 7E

```
                                                        961
GGT TCA AAG AAG ACT CAG GGA GAG AAA TTT
GLY SER LYS LYS THR GLN GLY GLU LYS PHE
                                                       1051
TTG GAT GTG GTG AAA TTA TTA TAC AAT GAG
LEU ASP VAL VAL LYS LEU LEU TYR ASN GLU
                                                       1141
CAA GTT CAG ATA AAC CCT ACA CCT TTC CAA
GLN VAL GLN ILE ASN PRO THR PRO PHE GLN
                                                       1231
TTG ACT GTT TAT CCT CAT GGT TTG TTA AAT
LEU THR VAL TYR PRO HIS GLY LEU LEU ASN
                                                       1321
CAC TTT AAA GAT CCA CAA TAC CCA GTT TGG
HIS PHE LYS ASP PRO GLN TYR PRO VAL TRP
                                                       1411
TCA CTC AAT GTT TTA GCT AGA TTT ACA GAT
SER LEU ASN VAL LEU ALA ARG PHE THR ASP
                                                       1501
AGT ACT ACT GAG AAT GTG GTG AAT CTG TCA
SER THR THR GLU ASN VAL VAL ASN LEU SER
                                                       1591
GAT CCG TCC CAG GGT GGT GGG ATC AAA ATT
ASP PRO SER GLN GLY GLY GLY ILE LYS ILE
                                                       1681
TCA GAC TCA GTT GGT CAA CAA ATT AAA GTT
SER ASP SER VAL GLY GLN GLN ILE LYS VAL
                                                       1771
ACT GCT TTG GCT TCT ATT TGT CAG ATG TTT
```

FIG. 7F

```
                                                          991
TTC  TTG  ATT  CAT  TCT  GCA  GAT  TGG  CTT  ACT
PHE  LEU  ILE  HIS  SER  ALA  ASP  TRP  LEU  THR
                                                         1081
CAG  TTT  GCT  GTT  CAA  GGG  TTG  TTG  AGA  TAC
GLN  PHE  ALA  VAL  GLN  GLY  LEU  LEU  ARG  TYR
                                                         1171
CAG  GGG  GGA  TTG  ATC  TGT  GCT  ATG  GTT  CCT
GLN  GLY  GLY  LEU  ILE  CYS  ALA  MET  VAL  PRO
                                                         1261
TGC  AAT  ATT  AAC  AAT  GTG  GTT  AGA  ATA  AAG
CYS  ASN  ILE  ASN  ASN  VAL  VAL  ARG  ILE  LYS
                                                         1351
GAA  TTG  ACA  ATT  AGA  GTT  TGG  TCA  GAA  TTA
GLU  LEU  THR  ILE  ARG  VAL  TRP  SER  GLU  LEU
                                                         1441
TTG  GAG  TTG  CAT  GGA  TTA  ACT  CCT  CTT  TCT
LEU  GLU  LEU  HIS  GLY  LEU  THR  PRO  LEU  SER
                                                         1531
AAT  TAT  GAA  GAT  GCA  AGA  GCA  AAG  ATG  TCT
ASN  TYR  GLU  ASP  ALA  ARG  ALA  LYS  MET  SER
                                                         1621
ACT  CAT  TTT  ACT  ACT  TGG  ACA  TCT  ATT  CCA
THR  HIS  PHE  THR  THR  TRP  THR  SER  ILE  PRO
                                                         1711
ATT  CCA  GTT  GAC  CCA  TAT  TTT  TTC  CAA  ATG
ILE  PRO  VAL  ASP  PRO  TYR  PHE  PHE  GLN  MET
                                                         1801
TGT  TTT  TGG  AGA  GGA  GAT  CTT  GTC  TTT  GAT
```

FIG. 7G

```
                                                          1831
TTT CAA GTT TTT CCC ACC AAA TAT CAT TCA
PHE GLN VAL PHE PRO THR LYS TYR HIS SER
                                                          1921
TTA AAG CAA GCA ACT ACT GCT CCT TGT GCA
LEU LYS GLN ALA THR THR ALA PRO CYS ALA
                                                          2011
ACT CCT TAC AGA GTG AAC AGG TAT ACA AAG
THR PRO TYR ARG VAL ASN ARG TYR THR LYS
                                                          2101
AGA TTG ACC TCT CCT TCT AAC GTT GCT TCC
ARG LEU THR SER PRO SER ASN VAL ALA SER
                                                          2191
CAT GCT ATG GAT GTT ACT ACA CAA GTT GGA
HIS ALA MET ASP VAL THR THR GLN VAL GLY
                                                          2281
GTT GGT ATA ACA ACC ATG AAA GAT TTG AAA
VAL GLY ILE THR THR MET LYS ASP LEU LYS
                                                          2371
ACA ACA ATT GAG GAT CCA GTT TTA GCA AAG
THR THR ILE GLU ASP PRO VAL LEU ALA LYS
                                                          2461
ATG TCC ATC TAC AAG TTT ATG GGA AGG TCT
MET SER ILE TYR LYS PHE MET GLY ARG SER
                                                          2551
TTG TCT TCA ACC TCT AAT CCT CCT CAT GGT
LEU SER SER THR SER ASN PRO PRO HIS GLY
```

FIG. 7H

```
                                                        1861
GGT AGA TTA CTG TTT TGT TTT GTT CCT GGC
GLY ARG LEU LEU PHE CYS PHE VAL PRO GLY
                                                        1951
GTA ATG GAT ATT ACA GGA GTG CAG TCA ACT
VAL MET ASP ILE THR GLY VAL GLN SER THR
                                                        2041
TCA GCA CAT CAG AAA GGT GAG TAC ACT GCC
SER ALA HIS GLN LYS GLY GLU TYR THR ALA
                                                        2131
CAT GTC AGA GTG AAT GTT TAT CTT TCA GCA
HIS VAL ARG VAL ASN VAL TYR LEU SER ALA
                                                        2221
GAT GAT TCT GGA GGT TTT TCA ACA ACA GTT
ASP ASP SER GLY GLY PHE SER THR THR VAL
                                                        2311
GGA AAA GCT AAC AGA GGG AAA ATG GAT GTT
GLY LYS ALA ASN ARG GLY LYS MET ASP VAL
                                                        2401
AAA GTA CCT GAG ACA TTT CCT GAA TTG AAA
LYS VAL PRO GLU THR PHE PRO GLU LEU LYS
                                                        2491
CAT TTC TTG TGC ACT TTT ACA TTC AAT TCA
HIS PHE LEU CYS THR PHE THR PHE ASN SER
                                                        2581
TTG CCA TCA ACA CTG AGG TGG TTT TTC AAC
LEU PRO SER THR LEU ARG TRP PHE PHE ASN
```

FIG. 7I

```
                                                      1891
AAT GAG CTA ATA GAT GTT TCT GGA ATC ACA
ASN GLU LEU ILE ASP VAL SER GLY ILE THR
                                                      1981
TTG AGA TTT CGT GTT CCC TGG ATT TCT GAC
LEU ARG PHE ARG VAL PRO TRP ILE SER ASP
                                                      2071
ATT GGG AAG CTT ATT GTG TAT TGT TAT AAC
ILE GLY LYS LEU ILE VAL TYR CYS TYR ASN
                                                      2161
ATT AAC TTG GAA TGT TTT GCT CCT CTT TAT
ILE ASN LEU GLU CYS PHE ALA PRO LEU TYR
                                                      2251
TCT ACA GAA CAG AAT GTT CCA GAT CCC CAA
SER THR GLU GLN ASN VAL PRO ASP PRO GLN
                                                      2341
TCA GGA GTA CAA GCA CCT GTG GGA GCT ATC
SER GLY VAL GLN ALA PRO VAL GLY ALA ILE
                                                      2431
CCT GGA GAA TCC AGA CAT ACA TCA GAT CAT
PRO GLY GLU SER ARG HIS THR SER ASP HIS
                                                      2521
AAT AAT AAA GAG TAC ACA TTT CCT ATA ACC
ASN ASN LYS GLU TYR THR PHE PRO ILE THR
                                                      2611
TTG TTT CAG TTG TAT AGA GGG CCT TTA GAT
LEU PHE GLN LEU TYR ARG GLY PRO LEU ASP
```

FIG. 7J

```
                                    2641
CTG ACA ATT ATT ATT ACA GGA GCA ACT GAT
LEU THR ILE ILE ILE THR GLY ALA THR ASP
                                    2731
AAG GAG TCA GCT TTG TCT ATT GAC TAC AAA
LYS GLU SER ALA LEU SER ILE ASP TYR LYS
                                    2821
CCA TGG TAT TCT TAT TTA TAT GCT GTG TCT
PRO TRP TYR SER TYR LEU TYR ALA VAL SER
                                    2911
ATT GCA AAT TAC AAT CAT TCT GAT GAA TAC
ILE ALA ASN TYR ASN HIS SER ASP GLU TYR
                                    3001
CCA TTG AAC TCA AAT GCC ATG TTA TCC ACT
PRO LEU ASN SER ASN ALA MET LEU SER THR
                                    3091
TCA GAG GAA GAT AAA AGA TTT GAG AGT CAT
SER GLU GLU ASP LYS ARG PHE GLU SER HIS
                                    3181
TAT GCT CAG GAA GAA TTG TCA AAT GAA GTA
TYR ALA GLN GLU GLU LEU SER ASN GLU VAL
                                    3271
ACT GAG GAG CAT GAA ATA ATG AAG TTT TCC TGG
THR GLU GLU HIS GLU ILE MET LYS PHE SER TRP
```

FIG. 7K

```
                                                2671
GTA GAT GGC ATG GCC TGG TTC ACT CCA GTA
VAL ASP GLY MET ALA TRP PHE THR PRO VAL
                                                2761
ACT GCT CTT GGA GCT GTC AGA TTT AAC ACA
THR ALA LEU GLY ALA VAL ARG PHE ASN THR
                                                2851
GGA GCA CTG GAT GGT TTG GGT GAC AAG ACA
GLY ALA LEU ASP GLY LEU GLY ASP LYS THR
                                                2941
TTG TCT TTT AGT TGT TAT TTG TCT GTC ACA
LEU SER PHE SER CYS TYR LEU SER VAL THR
                                                3031
GAA TCA ATG ATG AGC AGA ATT GCA GCT GGA
GLU SER MET MET SER ARG ILE ALA ALA GLY
                                                3121
ATA GAA TGC AGG AAG CCA TAT AAA GAA CTG
ILE GLU CYS ARG LYS PRO TYR LYS GLU LEU
                                                3211
CTT CCA CCC CCT AGG AAA ATG AAG GGA CTG
LEU PRO PRO PRO ARG LYS MET LYS GLY LEU
```

FIG. 7L

```
                                            2701
GGT CTT GCC GTT GAT ACT CCT TGG GTA GAG
GLY LEU ALA VAL ASP THR PRO TRP VAL GLU
                                            2791
AGG AGA ACA GGG AAC ATT CAG ATT AGA TTA
ARG ARG THR GLY ASN ILE GLN ILE ARG LEU
                                            2881
GAT TCT ACA TTT GGA TTG GTT TCT ATT CAG
ASP SER THR PHE GLY LEU VAL SER ILE GLN
                                            2971
GAA CAA TCA GAG TTT TAT TTT CCC AGA GCT
GLU GLN SER GLU PHE TYR PHE PRO ARG ALA
                                            3061
GAC TTG GAG TCA TCA GTG GAT GAT CCT AGA
ASP LEU GLU SER SER VAL ASP ASP PRO ARG
                                            3151
AGA TTA GAA GTT GGG AAA CAA AGA CTC AAG
ARG LEU GLU VAL GLY LYS GLN ARG LEU LYS
                                            3241
TTT TCA CAA GCC AAA ATT TCT CTT TTT TAT
PHE SER GLN ALA LYS ILE SER LEU PHE TYR
```

FIG. 8A

```
              110       120       130       140       150       160       170       180
         TAGAAAGAGTCCCATTTATCATCACATTGATAAAACCATGATTAATTTTCCTGCAGCTATGCCCTTTTCTAAAGCT
           ArgLysSerProIleTyrHisHisIleAspLysThrMetIleAspPheProAlaAlaMetProPheSerLysAla*

190       200       210       220       230       240       250       260       270
         GAAATTGATCCAATGGCTGTGATGTTACTAAGTATTCATTACCTATTGTAGAAGAACCAGAGGATTATAAAGAGGCTTCAATTTTTAT
           GluIleAspProMetAlaValMetLeuSerLysTyrSerLeuProIleValGluGluProGluAspTyrLysGluAlaSerIlePheTyr 280       290       300       310       320       330       340       350       360
         CAAAATAAAATAGTGGGTAAGACTCAGTTGTTTAGATCTTGATTTTTAGATATGGCCATTACAGGGCCCCAGGAATTGATGCTATC
           GlnAsnLysIleValGlyLysThrGlnLeuValValAspPheLeuAspMetAlaIleThrGlyAlaProGlyIleAspAlaIle 370       380       390       400       410       420       430       440       450
         AACATGGATTCATCTCCTAGATTTCCTTATGTCCAAGGGAAGTTGACCAAAAGAGATTTAATTTGGTTGGATGAAAATGGTTTATTGCTG
           AsnMetAspSerSerProArgPheProTyrValGlnGlyLysLeuThrLysArgAspLeuIleTrpLeuAspGluAsnGlyLeuLeu 460       470       480       490       500       510       520       530       540
         GGAGTTCATCCAAGATTGGCTCAGAGAATCTTATTCAATACTGTCATGATGGAAAATTGTTCTGATTTGGATGTTGTTTTACAACCTGT
           GlyValHisProArgLeuAlaGlnArgIleLeuPheAsnThrValMetMetGluAsnCysSerAspLeuAspValValPheThrThrCys
```

FIG. 8B

```
          550        560        570        580        590        600        610        620        630
CCAAAAGATGAATTGAGACCATTAGAGAGAAAGTGTTGGAATCAAAAACAAGAGCTATTGATGCTTGTCCTCTGGATTACTCAATTTTGTGC
ProLysAspGluLeuArgProLeuLysValLeuGluSerLysThrArgAlaIleAspAlaCysProLeuAspTyrSerIleLeuCys 640        650        660        670        680        690        700        710        720
CGAATCTATTGGGGTCCAGCTATTAGTTATTTCATTTGAATCCAGGTTTCCATACAGGTGTTGCTATTGGCATAGATCCTGATAGACAG
ArgMetTyrTrpGlyProAlaIleSerTyrPheHisLeuAsnProGlyValAlaIleGlyIleAspProAspArgGln 730        740        750        760        770        780        790        800        810
TGGGATGAATTATTTAAAACAATGATAAGATTCGGAGATGTTGGTCTTGATTTGATTTCTCTGCTTTTAGATGCTAGTCTTAGTCCATTT
TrpAspGluLeuPheLysThrMetIleArgPheGlyAspValGlyLeuAspLeuIleSerLeuLeuAspAlaSerLeuSerProPhe 820        830        840        850        860        870        880        890        900
ATGATTAGAGAAGCAGGTAGAATCATGAGTGAACTCTGGAACTCCATCCCATTTTGGCACAGCTCTTATCAATACTATCATTATTCC
MetIleArgGluAlaGlyArgIleMetSerGluLeuTrpAsnSerIleProPheTrpHisSerSerTyrGlnTyrHisTyrTyrSer 910        920        930        940        950        960        970        980        990
AAGCATTTGCTGTATAACTGTGTTTACCATGTCTGTGGTTCAATGCCCTCTGGGTCTCCTCCTTGTACAGCTTTGCTAAATTCAATTATTAAT
LysHisLeuLeuTyrAsnCysCysTyrHisValCysCysSerMetProSerGlySerProCysThrAlaLeuLeuAsnSerIleIleAsn 1000       1010       1020       1030       1040       1050       1060       1070       1080
AATGTCAATTTGTATTATGTGTTTCCAAGATATTTGGAAAGTCTCCAGTTTTCTTTTGTCAGGCTTTGAAGATTCTCTGTTATGGAGAT
AsnValAsnLeuTyrTyrValPheSerLysIlePheGlyLysSerProValPheCysGlnAlaLeuLysIleLeuCysTyrGlyAsp
```

FIG. 8C

```
           1090      1100      1110      1120      1130      1140      1150      1160      1170
GATGTTTTAATAGTTTTCTCTCGAGATGTTCAGATTGATAATCTTCATTGATTGGACAAAAAATTGTAGATGAGTTAAGAAACTTGGC
AspValLeuIleValPheSerArgAspValGlnIleAspAsnLeuAspLeuIleGlyGlnLysIleValAspGluPheLysLysLeuGly 1180      1190      1200      1210      1220      1230      1240      1250      1260
ATGACAGCTACTTCTGCTGACAAGAATGTACCTCAGCTGAAACCAGTTTCGGAATTGACTTTTCTCAAAAGATCTTTCAATTGGTAGAG
MetThrAlaThrSerAlaAspLysAsnValProGlnLeuLysProValSerGluLeuThrPheLeuLysArgSerPheAsnLeuValGlu 1270      1280      1290      1300      1310      1320      1330      1340      1350
GATAGAATTAGACCTGCAATTTCGGAAAAACAATTGGTCTTTAATAGCATGGCAGAAGTAACGCTGAGTTTGAGCCAGAATTTAGAA
AspArgIleArgProAlaIleSerGluLysThrIleTrpSerLeuIleAlaTrpGlnSerAsnAlaGluPheGluGlnAsnLeuGlu 1360      1370      1380      1390      1400      1410      1420      1430      1440
AATGCTCAGTGGTTTGCTTTTATGCATGGCTATGAGTTTATCAGAAATTTTATTTGTTCAGTCCTGTTTGGAGAAAGAGATCATA
AsnAlaGlnTrpPheAlaPheMetHisGlyTyrGluPheIleArgAsnPheIleCysSerLeuPheGlyGluLysGluMetIle *

1450      1460      1470      1480      1490      1500      1510      1520      1530
GAATACAGACTTAAATCTTATGATTGGTGGAGAATGAGATTTTATGACCAGTGTTTCATTTGTGACCTTTCATGATTGTTTAAACAAAT
GluTyrArgLeuLysSerTyrAspTrpTrpArgMetArgPheTyrAspGlnCysPheIleCysAspLeuSer * PheVal * ThrAsn 1540      1550      1560      1570      1580      1590
TTTCTTAAAATTTCTGAGGTTTGTTTATTTCTTTTATCAGTAAATAAAAAAAAAAAAAAAA
PheLeuLysIleSerGluValCysLeuPheLeuLeuSerValAsnLysLysLysLysLys
```

METHODS OF DETECTING HEPATITIS A VIRUS

GOVERNMENT SUPPORT

The work described herein was supported by the National Institute of Allergy and Infectious Diseases and the National Cancer Institute, Department of Health and Human Services.

RELATED APPLICATIONS

This application is a continuation-in-part of application Ser. No. 07/256,135, filed Oct. 6, 1988, now abandoned, which is a continuation of application Ser. No. 06/654,942, filed Sep. 27, 1984, now abandoned, which is a continuation-in-part of application Ser. No. 06/537,911, filed Sep. 30, 1983, now abandoned.

TECHNICAL FIELD

This invention is in the field of microbiology and more specifically relates to recombinant DNA techniques for producing genetically-engineered microorganisms.

BACKGROUND ART

Hepatitis A virus (HAV) is an important cause of human hepatitis. In the United States it has been estimated that over 100,000 clinical cases occur annually. HAV continues to be endemic in underdeveloped areas of the world where infections usually occur in children, and nearly all of the young adult population have antibody to HAV (anti-HAV). Clinical hepatitis A and prevalence of anti-HAV are decreasing in industrialized nations, resulting in increasing numbers of adults susceptible to infection.

HAV is spread predominately by the fecal-oral route. Spread of hepatitis A is usually associated with overcrowding, poor hygiene, or breakdown in normal sanitary conditions. Contaminated food or water are frequent vehicles of spread. Groups at high risk include institutionalized persons, contacts of very young children in day-care centers, male homosexuals, consumers of raw shellfish and travelers to areas of the world where the disease is endemic.

The host range of HAV is limited to man, apes (especially the chimpanzee), and several species of New World monkeys. The incubation period for natural infections with HAV in man ranges from 15 to 45 days and averages 25 days. The first serological marker to appear is HAV in the stool, which often occurs 7–10 days before the onset of symptoms (dark urine or jaundice). Viral replication appears to be limited to the liver and excretion into the stool, where the highest levels of infectious virus are found, probably occurs via the biliary system. The virus is often rapidly cleared after the onset of symptoms and becomes undetectable in the stool. However, in some individuals, HAV can be found in the stool for longer periods.

Radioimmunoassay is a sensitive technique for detecting HAV in stool samples during the period of excretion, but it is not used in most clinical laboratories because assays for anti-HAV in serum (described below) are more easily performed and accurate. Therefore, patients with hepatitis A are usually considered as potentially infectious for up to two weeks after the onset of jaundice. Hepatitis A usually resolves with weeks, but occasionally illness may persist for several months. Mortality from hepatitis A or associated chronic liver disease are very unusual occurrences. Anti-HAV is almost always detectable in serum when symptoms begin. Because of this, diagnosis of hepatitis A is established using commercially available assays that are based on detection of anti-HAV IgM. An example of such an assay is that produced and marketed by Abbott Laboratories, North Chicago, Ill. under the name HAVAB-M™ kit. The development of anti-HAV IgG appears to be associated with lifelong immunity to HAV, for which only one serotype has been described. Temporary protection against hepatitis A for susceptible individuals can be achieved by injection of immune serum globulin, but at present there is no vaccine available.

The 27 nm virion of HAV was first visualized in 1973. See, Feinstone, S. M., Kapikian, A. Z. & Purcell, R. H. (1973) *Science* 182, 1026–1028. It was first isolated in tissue culture in 1979. See, Provost, P. J. & Hilleman, M. R. (1979) *Proc. Soc. Exp. Biol. Med.* 160, 213–221. Recently, HAV has been classified as a picornavirus. See, Coulepis, A. G., Locarnini, S. A., Westaway, E. G., Tannock, G. A. & Gust, I. D. (1982) *Intervirology* 18, 107–127.

HAV has a sedimentation coefficient of approximately 160 S and a primary buoyant density of 1.34 g/ml in CsCl. Virion capsid polypeptides of $M_r$= 32,000, 26,000, 22,000 and 10,000 have been described. The single-stranded infectious RNA has a molecular weight of about $2.5\times10^6$; various genome lengths (between 6700–8100 nucleotides) have been reported. It contains poly(A), presumably at the 3' terminus. By analogy with other picornaviruses, the RNA should contain an open reading frame of about 6500 nucleotides which directs synthesis of a polyprotein that is post-translationally cleaved into virion proteins. These include the four capsid proteins, a peptide linked to the 5' end of the genome (VPg), an RNA-dependent RNA polymerase, and a protease. Putnak, J. R. & Phillips, B. A. (1981) *Microbiol. Rev.* 45, 287–315; Kitamura, N., Semler, B. L., Rothberg, P. G., Larsen, G. R., Adler, C. J., Dorner, A. J., Emini, E. A., Hanecak, R., Lee, J. J., van der Werf, S., Anderson, C. W. & Wimmer, E. (1981) *Nature* (London) 291, 547–553; Racaniello, V. R. & Baltimore, D. (1981) *Proc. Natl. Acad. Sci. USA* 78, 4887–4891; and, Nomoto, A., Omata, T., Toyoda, H., Kuge, S., Horie, H., Kataoka, Y., Genba, Y., Nakano, Y. & Imura, N. (1982) *Proc. Natl. Acad. Sci. USA* 79, 5793–5797.

The genomes of wild-type HAV strain HM-175 and its cell culture-adapted (CC) variant have been cloned as cDNAs in front of the Sp6 promoter of a plasmid expression vector (Cohen et al J. Virol. 3:5364 (1989); Cohen et al J. Virol. 61:3035 (1987)). In vitro transcription of the cDNA clone of the CC variant produced an RNA which was infectious when transfected into cultured primary AGMK cells, and the resultant virus displayed the growth and attenuation phenotypes of the parent (Cohen et al J. Virol. 63:5364 (1989); Cohen et al, J. Virol. 61:3035 (1987)). Although RNA transfected from the wild-type cDNA clone was not infectious in these assays, certain chimeric genomes containing wild-type sequence in combination with the P2/P3 sequence of the CC variant were infectious (Cohen et al, J. Virol. 63:5364 (1989)). The construction and analysis of additional chimeric genomes from these two cDNA clones has been reported and it has been demonstrated that mutations in both the P2 and 5' noncoding region of the genome are capable of increasing the efficiency of virus growth in vitro (Emerson et al, J. Virol. 65:4882 (1991). The effects of mutations in the 5' noncoding region are apparently host cell dependent, whereas those of the P2 region appear to be host cell independent.

DISCLOSURE OF THE INVENTION

This invention relates to the production of cDNA representing HAV viral sequences (HAV cDNA) (including, an infectious full-length, ligated cDNA clone of HAV HM-175 wild-type hepatitis A virus) and to methods for using such cDNA. The invention further relates to chimeric genomes of HAV and to methods of enhancing viral growth in vitro.

In one embodiment, HAV cDNA is produced by reverse transcribing HAV RNA and inserting the resulting cDNA molecule into a recombinant DNA vector. Appropriate cells are then transformed with the recombinant DNA vector, cloned and grown under conditions sufficient for production of HAV cDNA. This cDNA can then be harvested from the clonal cell culture and used, as is, or further modified for certain applications.

In a particular embodiment, bacteria are modified by genetic engineering techniques to make such bacteria capable of producing HAV double-stranded complementary DNA (ds cDNA). In this method, HAV single-stranded (ss) RNA is reverse transcribed to provide HAV ss cDNA which is extended to ds cDNA and then inserted into a bacterial plasmid to create a chimeric plasmid. The chimeric plasmid containing the ds cDNA is then inserted into bacterial cells by transforming the bacterial cells with the chimeric plasmid. Bacterial cells which have been so transformed can then be cloned and clonal cell lines grown in cell culture to replicate the chimeric plasmid. The HAV ds cDNA can then be recovered by enzymatically cleaving it from replicated chimeric plasmids.

This method provides for the microbiological production of relatively large quantities of HAV cDNA at reasonable costs. The cDNA, in turn, can be employed in assays for the detection of HAV since HAV cDNA will bind specifically to HAV RNA. Such assays can be performed quickly and easily and they offer the potential for being extremely sensitive and specific for HAV virus detection.

HAV cDNA can also be employed in the production of either HAV antigen or antibodies to such an antigen. In these methods, HAV cDNA is produced as described above. For antigen production, HAV cDNA capable of directing antigen synthesis is selected and inserted into cells capable of producing the antigen after which the cells are cultured under conditions suitable for antigen production and harvesting. An alternative method of antigen production is the synthesis of peptides, in vitro. The amino acid sequences of such peptides can be deduced from the determined nucleotide sequence of cloned HAV cDNA. For antibody production, harvested antigen is employed to immunize a host capable of producing antibodies to HAV. Monoclonal antibodies can be produced employing antibody-producing cells from the host and known techniques, such as the formation of hybridoma cell lines.

BRIEF DESCRIPTION OF THE DRAWINGS

FIGS. 7A thru 7L illustrate the nucleotide sequence of cloned HAV cDNA and predicted amino acid sequence from near the genome 5' terminus to the end of the area corresponding to the capsid protein region of poliovirus RNA; and FIGS. 8A, 8B and 8C illustrate the nucleotide sequence of cloned HAV cDNA and predicted amino acid sequence corresponding to the RNA polymerase region of poliovirus RNA and the genome 3' terminus.

BEST MODE FOR CARRYING OUT THE INVENTION

The methods described herein for producing HAV cDNA employ fundamental gene splicing techniques which have been described in the scientific literature. For example, U.S. Pat. No. 4,227,224, issued to Stanley N. Cohen and Herbert W. Boyer, on Dec. 2, 1980, describes many of these techniques. The teachings of the Cohen and Boyer patent, therefore are incorporated herein by reference.

Figure 1:
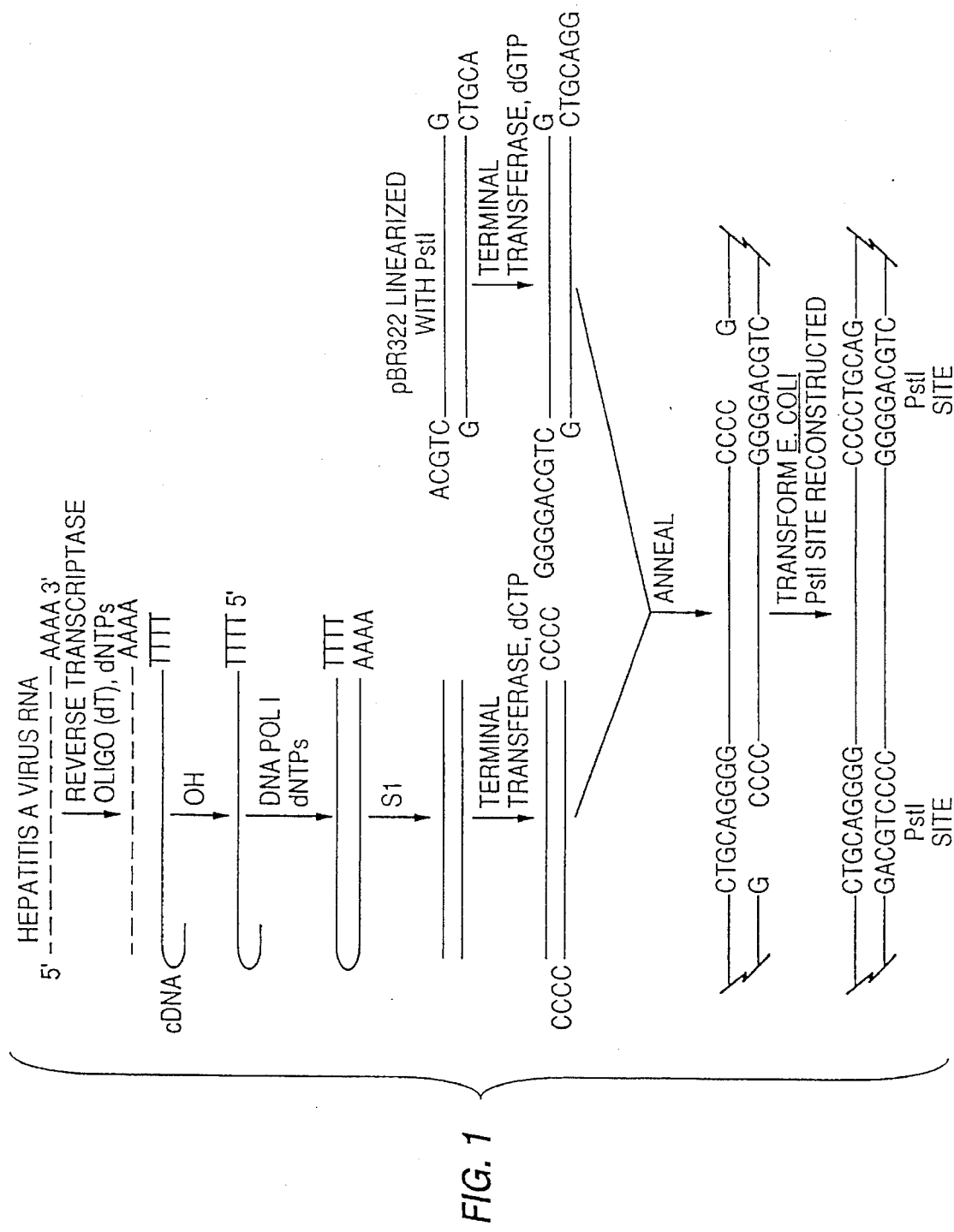
FIG. 1 is a schematic diagram illustrating the production of a bacterial chimeric plasmid containing HAV ds cDNA.

A more specific description of the techniques which can be employed in producing HAV ds cDNA will now be presented in conjunction with FIG. 1, a schematic diagram illustrating these techniques.

HAV was isolated from human stool during a family outbreak in Australia and passaged twice in marmosets. This virus, present in a homogenate of liver tissue, was injected intravenously into marmosets that were monitored for HAV production by immunofluorescent antibody analysis of biopsied liver tissue. The animals were killed when maximum immunofluorescence was reached, at which time their livers were removed, minced, frozen, and subsequently homogenized prior to purification of HAV. Alternatively, HAV can be purified directly from homogenates of human stool or HAV-infected tissue culture cells.

When isolated from liver or stool, the bulk of extraneous tissue and debris can be removed by low speed centrifugation. Disruption of cellular membranes that may bind or contain HAV can be accomplished by extensive hydrocarbon extraction. Micrococcal nuclease can be used to digest and eliminate non-encapsidated nucleic acids that might ultimately contaminate purified HAV RNA. The virus can be purified using successive steps of rate zonal and isopycnic density gradient centrifugation. Those skilled in the art will recognize that there are methods of purifying HAV that can be used alternatively or in conjunction with those above, such as gel filtration chromatography or ion-exchange chromatography.

HAV ss RNA can be extracted from the purified viral particles by digestion with sodium dodecyl sulfate (NaDodSO$_4$) and proteinase K, followed by extraction with phenol and chloroform/isoamyl alcohol. HAV ss RNA is then employed in the synthesis of HAV ds cDNA, as illustrated. Initially, the HAV ss RNA is reverse transcribed employing the enzyme reverse transcriptase, also known as RNA-dependent DNA polymerase. See Kacian, D. L. and Myers, J. C. (1976) *PNAS* 73: 2191–5. Typically, Tris-HCl buffer (pH 8.3), magnesium ions (Mg$^{++}$), potassium ions, dithioerythritol, sodium pyrophosphate, a ribonuclease inhibitor (RNasin), the four deoxynucleoside triphosphates (dATP, dCTP, dGTP and TTP), and at least one labeled deoxynucleoside triphosphate for monitoring the product are added to the reaction mixture. Oligo(dT) is also added as a primer which hybridizes to the poly(A) end of HAV RNA thereby providing a site for initiation of reverse transcription. The reaction mixture is incubated under conditions to allow the enzyme to synthesize a complementary ss DNA copy of the HAV genome starting from the 3' poly(A) end and continuing to the 5' end of the genome.

The RNA template is then removed with alkali. The cDNA molecules are then placed in another reaction mixture containing Tris-HCl buffer (pH 7.5), Mg$^{++}$, dithiothreitol, the 4-deoxynucleoside triphosphates, and the Klenow fragment of DNA polymerase I. This reaction mixture is maintained under conditions sufficient to allow the DNA polymerase I to extend the cDNA molecule, initiating synthesis at the snap-back formed at the 3' end of the molecule. In a typical example, the reaction mixture might be incubated at 37° for about 30 minutes, which is usually sufficient for formation of the second complementary DNA strand, as illustrated. See Humphries et al. (1978), *Nucleic Acids Res.*, 5:905–24.

S1 nuclease is then employed to cleave the loop at one end of the molecule. See Bhat and Piatigorsky (1975), *PNAS*, 7.6:3299–3303.

The ds cDNA can then be tailed with oligo(dC) at the 3' ends by employing terminal transferase and dCTP. See Boyer et al. (1977) in "Recombinant Molecules: Impact on Science and Society" (R. F. Beers and E. G. Bassett, eds.) pp 9–20, Raven, N.Y. This produces ds cDNA having poly(C) at both ends to serve as "sticky" ends in subsequent binding to a cleaved bacterial plasmid in order to form a recombinant DNA molecule. The tailed ds DNA can be filtered by gel chromatography, and the largest fragments are then pooled from the eluted fractions.

Plasmid pBR322 can be employed to illustrate chimeric plasmid formation. Plasmid pBR322 is a well characterized plasmid known to contain selectable markers. This plasmid contains one gene coding for tetracycline resistance as well as a gene coding for ampicillin resistance. Since the HAV ds cDNA sequences are inserted into the gene for ampicillin resistance, successfully transformed bacterial cells are ampicillin sensititve (Amp$^s$) and tetracycline resistant (Tet$^R$), the latter providing a marker for transformed cells.

Plasmid pBR322 is cleaved using the restriction enzyme Pst I at the gene coding for ampicillin resistance. The resulting linearized plasmid is then tailed with oligo(dG) employing the enzyme terminal transferase and dGTP to produce "sticky" ends on the linearized cleaved plasmid chains.

The oligo(dG) tailed plasmid DNA and the oligo(dC) tailed HAV ds cDNA are than hybridized in solution. This can be accomplished by mixing these DNA species in an equimolar ratio in 0.1M NaCl, heating for 3 minutes at 68° and then incubating at 42° for 2 hours. See Boyer, H. W., Bettlach, M., Bolivar, S. F. Rodriguez, R. L., Heyneker, H. L., Shine, J. and Goodman, H. M., (1977), "Recombinant Molecules: The Construction of Molecular Cloning Vehicles," in *Recombinant Molecules: Impact On Science and Society*, eds. Beers, R. F. and Bassett, E. C. pp. 9–20, Raven Press, N.Y.

The hybridized plasmid-HAV ds cDNA is then inserted into *E. coli* in order to reconstruct the Pst I site, to amplify the plasmid DMA, and to identify clones which contain recombinant plasmids. See Dagert, M. and Ehrlich, S. D. (1979), *Gene,* 23–28. Once the hybrid molecule is inserted, the single-stranded gap is repaired by the bacteria. This reconstruction provides two Pst I sites which the Pst I enzyme can later recognize and cleave to separate the HAV ds cDNA sequences from replicated plasmids.

*E. coli* cells transformed with the hybrid molecules can then be selected in the presence of tetracycline and later screened for ampicillin sensitivity. Those clones identified as Tet$^r$ Amp$^s$ can then be analyzed by using well-known techniques to obtain recombinant plasmids which are cleaved with pst I and sized by gel electrophoresis. Comparison of the electrophoretic pattern of digested hybrid plasmids with marker DNA fragments of known lengths indicates the lengths of the inserted cDNAs.

To establish the identity of a cloned cDNA, it can be hybridized to RNA from cells, including cells infected with HAV. Inserted cDNA can be isolated from plasmids by digestion with Pst I and electrophoresis in low melting point agarose. See, Cummings, I. W., et al., *Proc. Natl. Acad. Sci. USA* 77:1842–1846 (1980). The agarose gel containing the cDNA is melted and the cDNA recovered by extraction with phenol and with chloroform/isoamyl alcohol and then by precipitation with ethanol. Inserted cDNA can then be labeled with $^{32}$P by nick translation. See, Rigby, P. W. J., et al. *J. Molec. Biol.* 113: 237–251(1977). RNA can be isolated from cells, for example, by lysis with detergents, extraction with phenol and chloroform/isoamyl alcohol, and precipitation with ethanol. See Maniatis, T., et al., *Molecular Cloning*, Cold Spring Harbor Laboratory, Cold Spring Harbor, N.Y., 1982. This RNA can then be electrophoretically separated in agarose and transferred to nitrocellulose paper. See, Thomas, P.S., *Proc. Natl. Acad. Sci USA* 77:5201–5205(1980). The RNA on the nitrocellulose paper is hybridized with $^{32}$P-labeled cDNA insert in a sealed polyethylene bag. Autoradiography of the washed and dried paper reveals which RNA species the cloned cDNA species is derived from, since the labeled cDNA will hybridize to the RNA and appear as dark band(s) on the X-ray film which is exposed to the nitrocellulose paper. When the cloned cDNA species contains specific HAV sequences, the predominant RNA species identified will have the characteristic genomic length of picornaviral RMA (approximately 7500 nucleotides) and will be found only in RNA from HAV-infected cells. Direct screening of clones by colony hybridization is avoided since any probe prepared directly from purified HAV (labeled RNA or cDNA) might be as contaminated with nonviral sequences as the RNA template used for cloning.

Those skilled in the art will recognize, of course, that other materials and conditions can be employed other than those specifically described in the aforementioned embodiments. For example, it is clear that bacterial cells other than *E. coli* could be employed. For example, *B. subtilis* could also be employed as well as many other bacterial strains.

Similarly, although bacterial plasmids have been employed in producing HAV cDNA sequences, other recombinant DNA vectors could be employed. Examples of other recombinant DNA vectors include phages, animal viruses and yeast vectors. Hosts which allow the recombinant DNA vector to multiply are chosen, of course.

Figure 2:
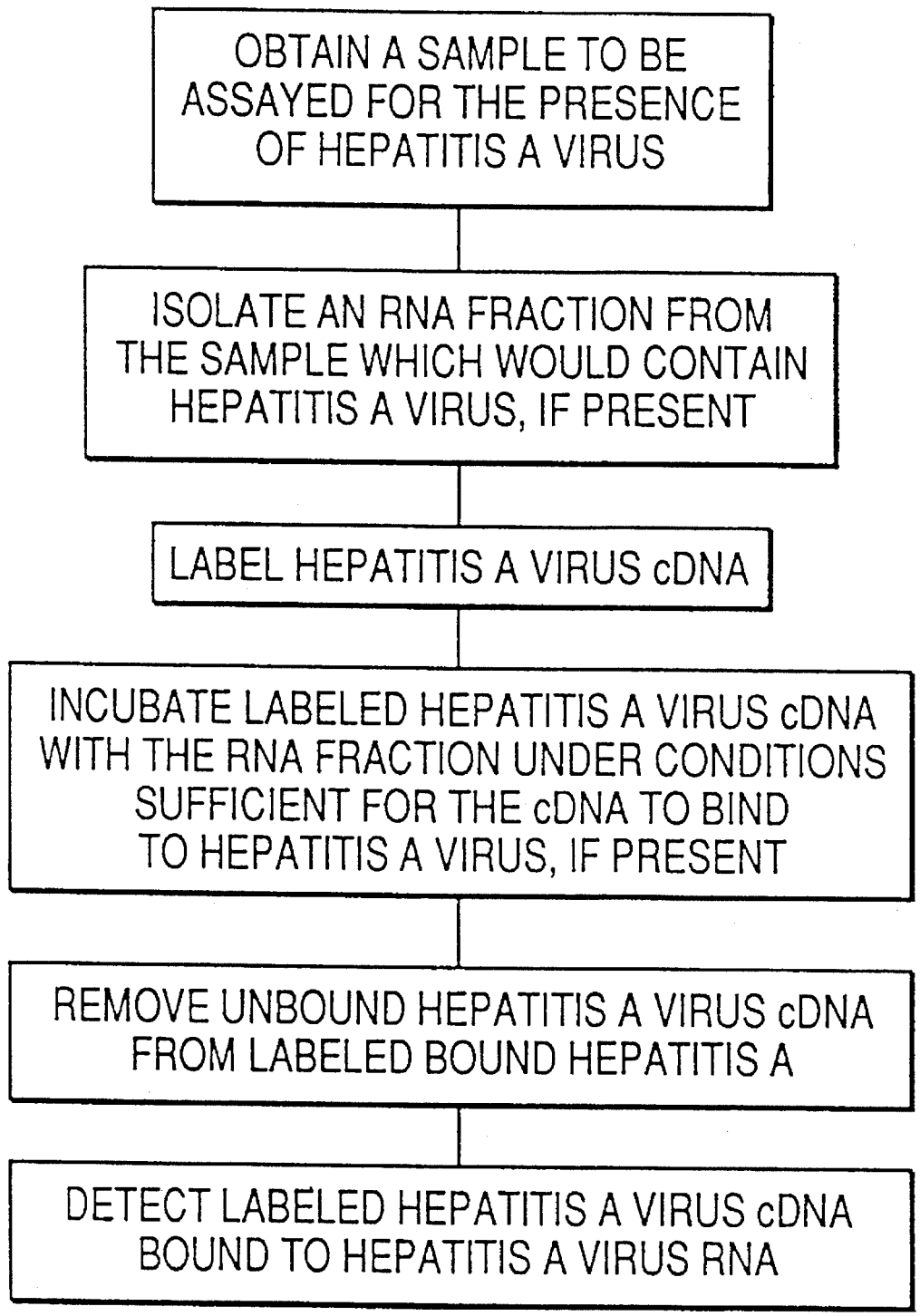
FIG. 2 is a block diagram illustrating one embodiment of an assay employing HAV cDNA produced according to the methods described herein.

One significant use for HAV cDNA produced according to this invention is in assays to detect the presence of HAV RNA. In a typical assay for HAV, for example, a patient sample, such as a stool specimen, can be assayed as illustrated in FIG. 2. The RNA fraction of the patient sample is first isolated, which can be done by phenol extraction and ethanol precipitation. This RNA fraction need not be pure, but it must be a fraction which would contain HAV RNA if HAV were present in the original sample. HAV cDNA is first labeled, e.g., with a radioactive material such as tritium, iodine, or $^{32}P$, and subsequently incubated with the RNA fraction under conditions to allow the labeled HAV cDNA to bind to HAV RNA, if present. After incubation, unbound labeled HAV cDNA is separated and bound labeled HAV cDNA is then detected in a scintillation counter or by other means.

Other patient samples, of course, such as a biopsy, might be employed. Additionally, the assay can be performed on other samples which might contain HAV, such as sewerage, water or shellfish suspected to be contaminated.

A solid-phase assay, although not illustrated, might be performed. Additionally, the label need not be a radioactive isotope, but might be an enzyme, optical label, etc.

In particular, it is believed that "dot blots" of stool extracts hybridized with HAV cDNA probe will provide a sensitive and easily performed assay for the presence of HAV. Such "dot blots" have been described. See Thomas, *PNAS* 77, 5201–5205 (1980).

Research laboratories studying HAV could employ HAV cDNA probes for detecting or quantitating HAV RNA in specimens such as cells or fluid from tissue culture, tissues and stool from experimentally infected primates, and specimens collected from patients. In the case of intact cells, the assay might be an in situ hybridization.

Another significant use for HAV cDNA produced according to this invention is in the production of HAV antigens. Antigenic proteins can be produced by reverse transcribing HAV RNA to provide cDNA, inserting the cDNA into a recombinant DNA vector and transforming cells in which said recombinant DNA vector can multiply. Transformed cells can then be cloned to produce a cell line capable of replicating the cDNA. The cell line can be cultured under conditions sufficient for the production of cDNA and cDNA can then be harvested from the cell culture. Specific cDNA could be selected and isolated which was capable of directing antigen synthesis in prokaryotic or eukaryotic cells and subsequently inserted into such cells so that these cells produce antigen. Alternatively, antigenic peptides can be synthesized in vitro. Cloned cDNA is produced and harvested as described above and its nucleotide sequence is determined. The amino acid sequences of such peptides are deduced from the nucleotide sequence of appropriate regions of the HAV genome (e.g., that coding for the capsid proteins). HAV antigen produced either by cells or in vitro could be used as an alternative source of the antigen component in the currently available immunoassays for anti-HAV in serum.

Antigen produced by the methods described above could be used to immunize a host, such as an animal, and cause that host to produce antibodies against HAV or a portion thereof. If desired, antibody producing cells could be employed to produce cell lines capable of producing monoclonal antibodies. Polyclonal or monoclonal antibodies would be useful reagents for laboratories involved in the study of HAV. Also, harvested antigen capable of eliciting protective anti-HAV in humans could be an effective means of vaccination. For example, a capsid protein produced from a suitable cell could possess sufficient antigenic properties for use in a vaccine against HAV, as has been demonstrated for a strain of foot and mouth disease virus (FMDV), another member of the picornavirus group. See, Kleid, D. G., et al. *Science* 214:1125–1129 (1981) . Neutralizing antibodies against FMDV have also been elicited using synthetic peptides as antigens. See, Bittle, J. L., et al., *Nature(London)* 298:30–33(1982).

The invention is further and more specifically illustrated by the following examples. One skilled in the art will appreciate from a reading of the Examples that while specific HAV variants capable of efficient growth in vitro are described in some detail, other variants having advantageous properties can be produced without undue experimentation, based on the disclosure provided.

EXAMPLE 1

Preparation of Hybridized Plasmid—HAV DS CDNA and Cloning in *E. Coli*

Preparation of HAV

The HM-175 strain of HAV was isolated from a family outbreak in Australia. See, Daemer, R. J., Feinstone, S. M., Gust, I. D. & Purcell, R. H. (1981) *Infect. Immun.* 32,388–393. HAV which had been passaged twice in marmosets (*Saguinus mystax* and *S. labiatus*) was inoculated into eight marmosets. A 20% wgt/vol suspension of HAV-infected liver in phosphate buffered saline was injected intravenously and animals were monitored by serum enzymes and immunofluorescence of liver biopsy. See, Mathiesen, L. R., Feinstone, S. M., Purcell, R. H. & Wagner, J. (1977) *Infect. Immun.* 18, 524–530. When maximum immunofluorescence was reached 10–14 days after inoculation, the marmosets were killed and their livers immediately removed, minced, frozen in liquid $N_2$, and stored at −70° C. until virus purification.

HAV was also passaged 6 times in marmosets and 19 times in secondary African green monkey kidney (AGMK) monolayers which were used as a source of RNA for hybridization. Infected cultures were harvested at 21 days when 100% of the cells exhibited maximal immunofluorescence.

Virus Purification. Minced marmoset livers were homogenized (40% wgt/wgt) in phosphate-buffered saline (PBS), 0.1% NP-40 in a Sorvall Omnimixer on ice. Particulate matter was removed by centrifugation at 13,000 g (pellets were re-extracted with PBS, 0.1% NP-40 and with trichlorotrifluoroethane/chloroform). The homogenate was concentrated in a Beckman Type 45Ti rotor at 40,000 rpm for 16 hr at 5° C. Pellets were resuspended in 10 mM Tris-HCl (pH 7.5), 0.1M NaCl, 0.1% NP-40 (TNN) and extensively extracted with trichlorotrifluoroethane and chloroform. Pooled aqueous layers were again concentrated in a Beckman Type 45Ti rotor at 40,000 rpm for 16 hr at 5° C. and pellets resuspended in 20 ml of TNN. The virus suspension was then treated with micrococcal nuclease (75 units/ml) in TNN, 1 mM $CaCl_2$ for 15 min at 20° C. The reaction was stopped by the addition of EGTA (ethylene glycol-bis[-aminoethyl ether] N,N,N',N'-tetraacetic acid) to 2 mM. See, Pelham, H. R. B. et al., *Eur. J. Biochem.* 67:247–256(1976). This preparation was centrifuged over an 8 ml cushion of 30% (wgt/wgt) sucrose in TNN in a Beckman SW27 rotor at 25,000 rpm for 16 hr at 5° C. The resulting pellet was resuspended in 0.8 ml TNN and layered over a 20–40% (wgt/wgt) gradient of sucrose in TNN, centrifuged in a Beckman SW27 rotor at 25,000 rpm for 4 hr at 5° C., and separated into 1 ml fractions. Those fractions with high reactivity in a solid phase radioimmunoassay (SPRIA) for HAV were pooled with solid CsCl added to a density of 1.36 g/ml and centrifuged in a Beckman Type 75Ti rotor at 60,000 rpm for 40 hr at 18° C. See, Purcell, R. H. et al., *J. Immunol.* 116:349–356(1976). Fractions with HAV by SPRIA were pelleted in a Beckman SW27 rotor for 17 hr at 5° C. The pellet was resuspended in 0.7 ml TNN and layered over a sucrose gradient as described above. The HAV-containing fractions were dialyzed against 10 mM Tris-CHl (pH 7.5), 0.1M NaCl, 1 mM ethylene diamine tetraacetic acid (EDTA). Direct electron microscopic examination of purified HAV particles revealed a homogeneous population of 27 nm virions.

RNA Extraction and Characterization. Suspensions of purified HAV were incubated at 37° for 15 rain with 500 ug/ml proteinase K, after which $NaDodSO_4$ was added to a concentration of 0.5% wgt/vol and incubation was continued for an additional 30 min. After extraction with phenol and then with chloroform-isoamyl alcohol (24 vol:1 vol), RNA was precipitated in ethanol, redissolved and, after removing a portion for analysis, reprecipitated. RNA was characterized by UV spectroscopy and agarose gel electrophoresis after denaturation with 1M glyoxal and 50% (vol/vol) dimethysulfoxide. See, McMaster, G. K. & Carmichael, G. G. (1977) *Proc. Natl. Acad. Sci. USA* 74, 4835–4838. HAV RNA contained a discrete band comigrating with poliovirus type 1 RNA (approximately 7440 nucleotides). See Kitamura, N., Semler, B. L., Rothberg, P. G., Larsen, G. R., Adler, C. J., Dorner, A. J., Emini, E. A.. Hanecak, R., Lee, J. J., van der Werf, S., Anderson, C. W. & Wimmer, E. (1981) *Nature (London)* 291, 547–553; Racaniello, V. R. & Baltimore, D. (1981) *Proc. Natl. Acad. Sci. USA* 78, 4887–4891; and Nomoto, A., Omata, T., Toyoda, H., Kuge, S., Horie, H., Kataoka, Y., Genba, Y., Nakano, Y. & Imura, N. (1982) *Proc. Natl. Acad. Sci. USA* 79, 5793–5797. Other portions were used to analyze template quality and optimal conditions for cDNA synthesis.

RNA for hybridization studies was prepared from uninfected and HAV-infected AGMK cells by isolation of total cytoplasmic RNA. See, Maniatis, T., Fritsch, E. F. & Sambrook, J. (1982) *Molecular Cloning* (Cold Spring Harbor Laboratory, Cold Spring Harbor, N.Y.). Polyadenylated RNA was isolated by oligo (dT) cellulose chromatography. See, Varmus, H. E., Quintrell, N. & Ortiz, S. (1981) *Cell* 25, 23–36. RNA was transferred to nitrocellulose paper after electrophoretic separation through agarose gels containing glyoxal-dimethylsulfoxide denatured RNA. See, Thomas, P.S. (1980) *Proc. Natl. Acad. Sci. USA* 77, 5201–5205.

The yield of virion RNA from eight marmoset livers was approximately 1.0 ug and the $A_{260}/A_{280}$ ratio was 2.0.

Preparation of cDNA Clones. RMAs from several sources of HAV and from poliovirus type 2 were compared for template quality in cDNA synthesis using alkaline agarose gel electrophoresis. RNAs (5 ug/ml or less) were incubated for 60 min at 42.5° C. in 10 ul containing 50 mM 4 Tris-HCl (pH 8.3); 10 mM $MgCl_2$; 50 mM KCl; 500 uM each: dATP, [$^{32}$P]dCTP (2 Ci/mmol), dGTP, and TTP; 0.4 mM dithioerythritol; 4 mM sodium pyrophosphate; 30 ug/ml oligo $(dT_{12-18})$; and 80 units/ml reverse transcriptase. Two reactions (cDNAs in FIG. 3, lanes b' and e') also contained 2000 units/ml RNasin. The resulting reverse transcripts from RNA templates are illustrated as follows in FIG. 3: lane a, HAV RNA derived from marmoset liver; lanes b and b', HAV RNA from AGMK cells; lane c, HAV RNA from human stool; lane d, HAV RNA from AGMK cells; lanes e and e', poliovirus type 2 RNA. HAV RNAs were isolated as described above except that derived from human stool (lane c) which was extracted from purified virus (a gift from S. Locarnini) and an earlier preparation from AGMK cells (lane d) using modifications of standard procedures. Migration of Hind III fragments in kilobases (kb) is indicated to the left of the figure.

Figure 3:
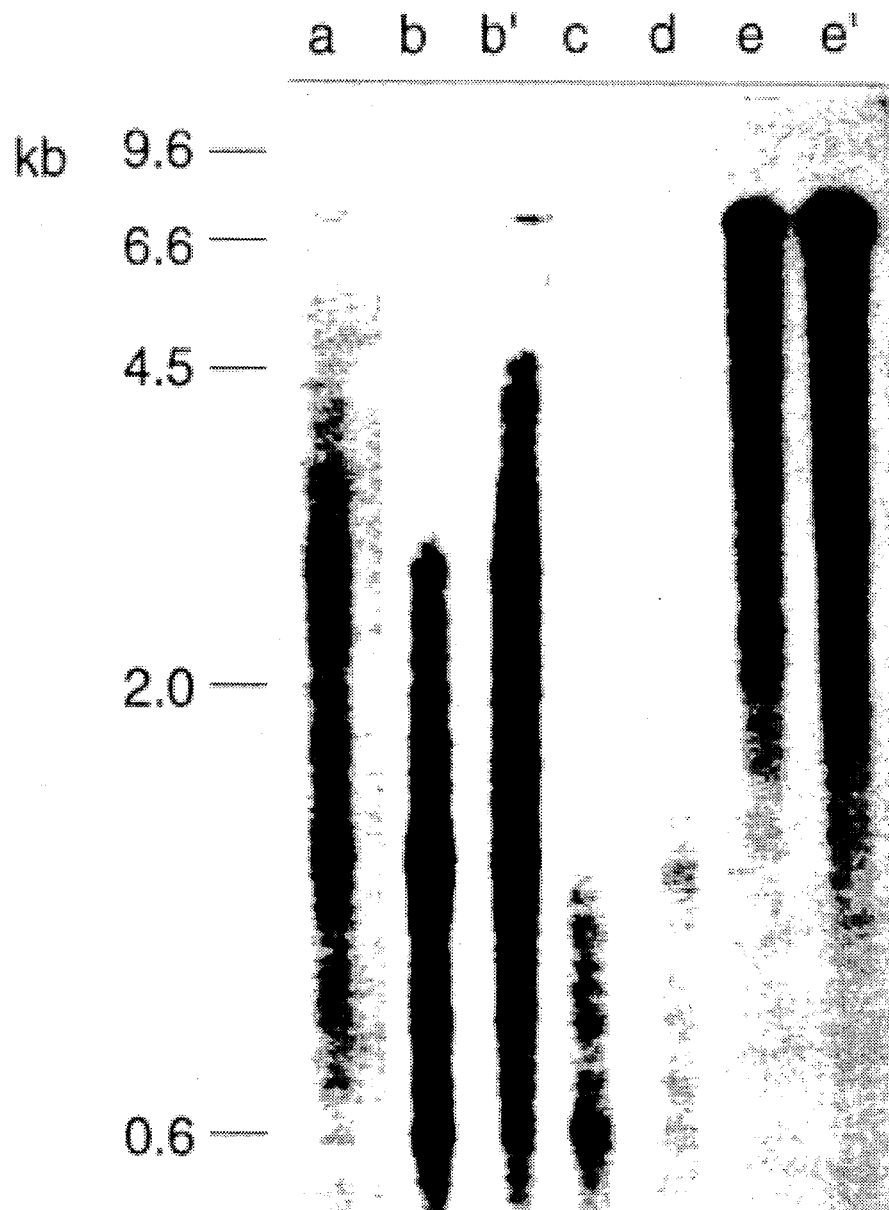
FIG. 3 shows the results of an alkaline agarose gel electrophoresis of cDNA from HAV RNA and poliovirus type 2 RNA.

HAV RNA derived from liver or AGMK culture yielded a series of transcripts ranging in size from slightly smaller than the longest poliovirus type 2 cDNA to less than 500 nucleotides (FIG. 3, lanes a, b, and b'; lanes e and e' show poliovirus type 2 cDNA). Presumably, degradation of HAV RNA prevented more extensive synthesis of reverse transcript approaching the expected full length of 7500 nucleotides. Other HAV cDNAs in FIG. 3 (lanes c and d) revealed evidence of more extensive RNA degradation, but all gave a similar banding pattern which was different from that of poliovirus cDNAs.

The effect of varying several chemical constituents and physical parameters on yield and length of HAV cDNA was analyzed by alkaline agarose gel electrophoresis and incorporation of [$^{32}$P]dCMP into trichloroacetic acid-precipitable product. Incubation for 30 min, with 120 units/ml reverse transcriptase, or with 100 mM KCl increased size and quantity of cDNA when compared to that shown in FIG. 3, lane b'. Denaturation of HAV RNA was not attempted because quantity was limited and, in earlier experiments, heat or methyl mercury treatment of poliovirus RNA decreased yield and size of cDNA.

Preparative conditions for HAV cDNA synthesis were based on findings in the analytical experiments described above. HAV RNA (0.8 ug) derived from marmoset liver served as a template for cDNA synthesis using reverse transcriptase (120 units/ml) for 30 min at 42.5° C. in 160 ul that contained 50 mM Tris-HCl (pH 8.3); 10 mM $MgCl_2$; 100 mM KCl; 500 mM each: dATP, [$^{32}$P]dCTP (0.025 Ci/mmol), dGTP, and TTP; 1 mM dithioerythritol; 4 mM sodium pyrophosphate; 30 ug/ml oligo$(dT_{12-18})$; and 2000 units/ml RNasin. After addition of EDTA to 20 mM, RNA-cDNA hybrids were isolated by phenol extraction, column chromatography and ethanol precipitation. The RNA template was hydrolyzed in 0.3 N NaOH, 0.7M NaCl and 5 mM EDTA for 2 hr at 37° C.

The second strand of cDNA was synthesized for 30 min at 37° C. using the large (Klenow) fragment of *E. coli* DNA polymerase I (28 units/ml) in 10 mM Tris-HCl (pH 7.5); 5 mM MgCl$_2$; 5 mM dithioerythritol; 50 uM each: dATP, [$^{32}$P]dCTP (0.45 Ci/mmol), dGTP, and TTP; and cDNA (1 ug/ml).

After phenol extraction, column chromatography, and ethanol precipitation, double-stranded cDNA (ds-cDNA) was digested for 1 hr at 37° C. using 10 units/ml nuclease S1 (0.1 units of S1 per ng ds-cDNA) in 30 mM NaOAc (pH 4.5), 0.3M NaCl, 3 mM ZnCl$_2$, and 5% vol/vol glycerol, followed by addition of EDTA to 35 mM, phenol and ether extraction, and dialysis against 10 m/4 Tris-HCl (pH 7.5) and 1 mM EDTA.

Figure 4:
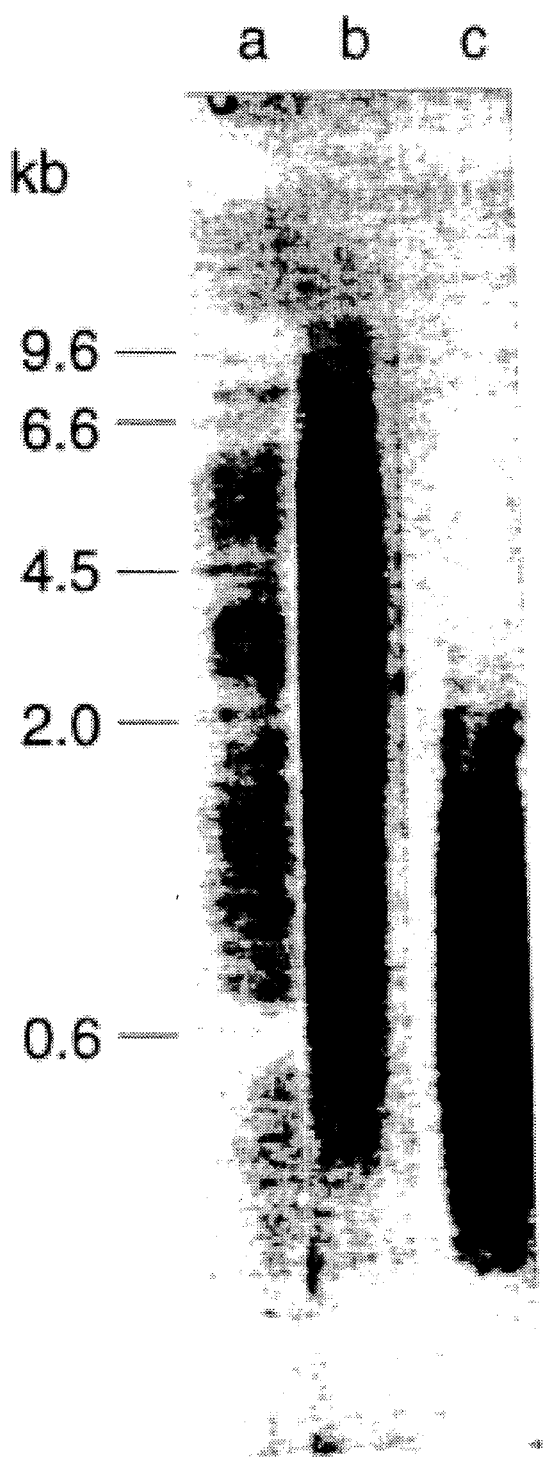
FIG. 4 illustrates the results of alkaline agarose gel electrophoresis of products of preparative HAV ds-cDNA synthesis.

Products of preparative HAV ds-cDNA synthesis were analyzed by alkaline agarose gel electrophoresis and the results are shown in FIG. 4: lane a, approximately 3 ng cDNA; lane b, approximately 2 ng ds-cDNA prior to nuclease S1 digestion; lane c, approximately 2 ng ds-cDNA after nuclease S1 digestion. Migration of Hind III fragments in kilobases (kb) is indicated to the left of the figure. A significant portion of HAV cDNA transcribed under preparative conditions was 3000–7500 nucleotides in length (FIG. 4, lane a). However, a wide size range of ds-cDNA molecules was produced (FIG. 4, lane b) and most of the preparation was less than 2000 nucleotides in length after S1 digestion (lane c).

Homopolymer tails of dCMP were added to ds-cDNA using 250 units/ml terminal deoxynucleotidyl transferase for 20 minutes at room temperature in 100 ul that contained 0.14M potassium cacodylate (pH 7.2), 1 mM CoCl$_2$ 0.2 mM dithioerythritol, 500 ug/ml nuclease-free bovine serum albumin, and 200 uM dCTP. After phenol extraction, 50% of ds-cDNA was ether-extracted and precipitated with ethanol.

The remaining tailed ds-cDNA was applied to a 3 ml column of Sepharose 4B in 20 mM Tris-HCl (pH 8.0), 0.6M NaCl and 2 mM EDTA. See, Maniatis, T., Fritsch, E. F. & Sambrook, J. (1982) *Molecular Cloning* (Cold Spring Harbor Laboratory, Cold Spring Habor, N.Y.). The first five 65 ul fractions containing ds-cDNA were pooled and precipitated in ethanol after the addition of 2 ug yeast tRNA.

Plasmid vector pBR322, cleaved at the Pst I site and tailed with dGMP, was annealed to equimolar amounts of both tailed ds-cDNA preparations and used to transform *E. coli* HB101 by standard procedures. See, Maniatis, T. et al., *Molecular Cloning* Cold Spring Harbor Laboratory, Cold Spring Harbor, N.Y., 1982.

Analysis of cDNA Clones. Clones containing putative HAV sequences were screened by cleaving recombinant plasmid preparations with Pst I and sizing by gel electrophoresis. Approximately 200 ng ds-cDNA was synthesized. Ten ng of ds-cDNA selected for large size by gel filtration yielded 232 tetracycline-resistant *E. coli* transformants. Cleavage with Pst 1 demonstrated inserts of 1000 base pairs or greater in 43 of the 232 recombinant plasmids, designated pHAV$_{LB}$. An additional 2710 clones were obtained from 9 ng of unfractionated ds-cDNA. From this group only pHAV$_L$ 1307 (described below) was extensively characterized.

Cloned cDNA inserts isolated from low melting point agarose were labelled by nick translation and used as probes in hybridization (i) to electrophoretically-separated RNA bound to nitrocellulose paper (described above) for establishing the identity of cloned cDNA species, (ii) to DNA bound to nitrocellulose paper after lysis of bacterial colonies in situ for further screening, and (iii) to restriction fragments of DNA resolved by electrophoresis and bound to nitrocellulose paper for confirmation of tentative restriction maps constructed on the basis of single and double enzyme digests.

Figure 5:
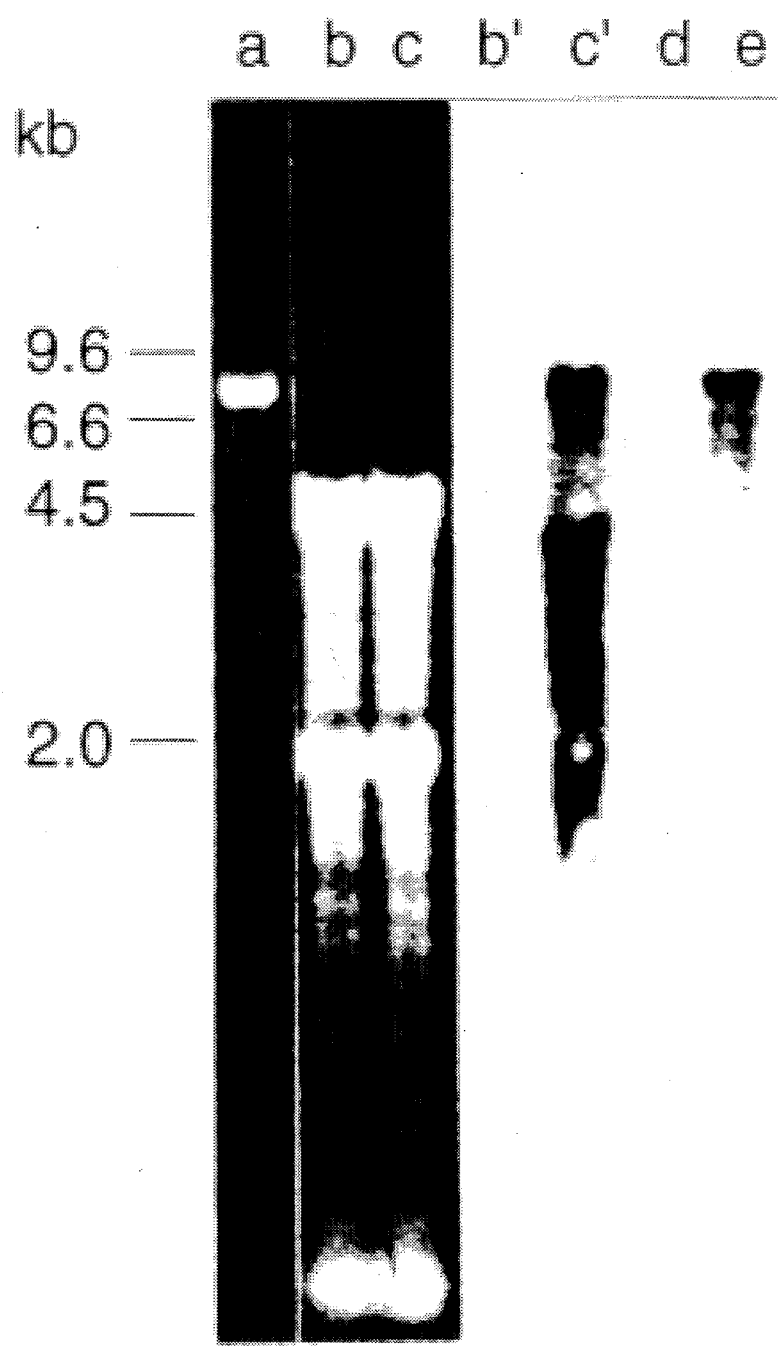
FIG. 5 illustrates the results of hybridization of cloned cDNA insert probe to HAV RNA.

The identity of inserted DNAs in recombinant plasmids was established by hybridization to RNA bound to nitrocellulose paper after gel electrophoresis and the results are shown in FIG. 5. Nucleic acids were denatured and electrophoresed; marker lanes (a–c) were removed and stained with 2 ug/ml ethidium bromide in 0.05 N NaOH for 40 min; followed by 0.5 ug/ml ethidium bromide in 40 mM Tris-HOAc (pH 7.8), 1 mM EDTA for 15 min and destaining in the same buffer for 15 min. Lanes b'–e were transferred to nitrocellulose paper and hybridized for 36 hr at 42° C. with 25 ng/ml [$^{32}$P]pHAV$_{LB}$39 insert (5×10$^8$ dpm/ug) in 50% vol/vol formamide; 0.75 M NaCl; 0.075M trisodium citrate; 50 mM sodium phosphate (pH 6.5); 0.2% NaDoSO$_4$; 100 ug/ml denatured sheared salmon sperm DNA; and 0.04% wgt/vol each: bovine serum albumin, polyvinylpyrollidone and Ficoll. Lane a contained 400 ng poliovirus type 2 RNA. Lanes b, b' and d contained cytoplasmic RNA from uninfected AGMK cells: lane b, 5 ug; lane b', 20 ug; and lane d, 1.5 ug, oligo(dT)-selected. Lanes c, c', and e contained cytoplasmic RNA from HAV-infected AGMK cells; lane c, 5 ug; lane c', 20 ug; and lane e, 1.5 ug, oligo(dT)-selected. Autoradiographic exposure for lanes b' and c' was one-eighth of that for lanes d and e. Migration of Hind III fragments in kilobases (kb) is indicated in FIG. 5.

A nick translated probe prepared from the insert of pHAV$_{LB}$39 specifically hybridized to RNA from HAV-infected AGMK cells (FIG. 5, lanes c' and e). Similar results were obtained when the inserts of pHAV$_{LB}$ 93 or pHAV$_{LB}$ 228 were used as probes. The predominant band identified had the size expected for genomic HAV RNA and comigrated with poliovirus type 2 RNA. Diffuse hybridization to lanes containing RNA from infected cells was probably due to RNA degradation. Nick translated pBR322 did not hybridize to any RNA species from either HAV-infected or uninfected AGMK cells, thereby eliminating the possibility that a small amount of pBR322 contaminating the insert probes was responsible for specific hybridization. None of the pHAV$_{LB}$ probes tested to date hybridized to poliovirus RNA.

Figure 6:
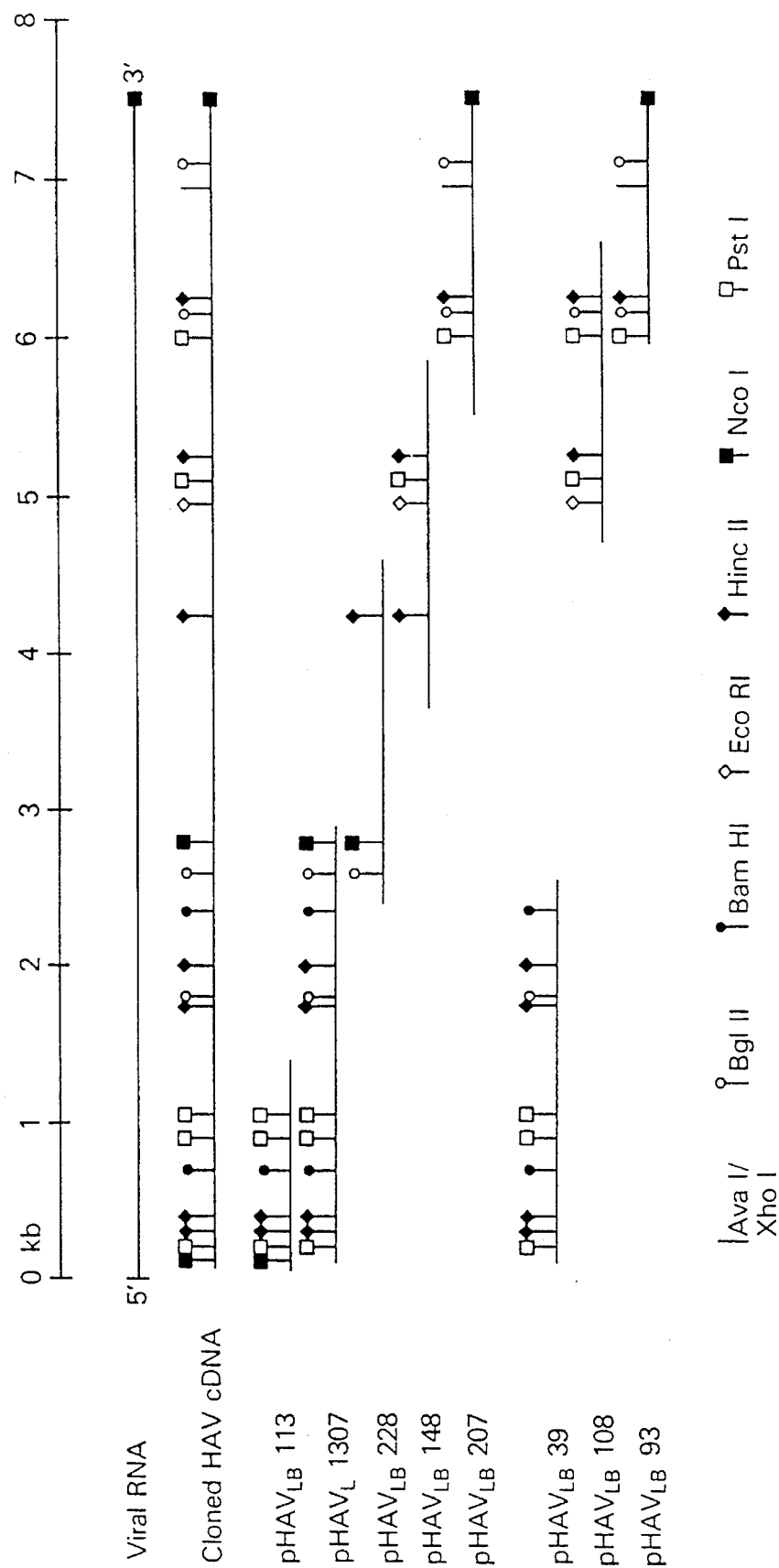
FIG. 6 is a restriction map of HAV cDNA clones prepared according to this invention.

The restriction map shown in FIG. 6 is based on data obtained from digests and on hybridization of labelled inserts to fractionated DNA. Viral RNA is estimated to be 7450 nucleotides in length excluding 3' poly(A) which is shown at the right (thicker line). A composite map of cloned HAV cDNA and positions of the inserts from clones pHAV$_{LB}$ 113, pHAV$_L$ 1307, pHAV$_{LB}$ 228, pHAV$_{LB}$ 148 and pHAV$_{LB}$ 207 are shown immediately below the viral RNA. Clones pHAV$_{LB}$ 113, pHAV$_{LB}$ 1307, pHAV$_{LB}$ 228, pHAV$_{LB}$ 148 and pHAV$_{LB}$ 207 were deposited with the American Type Culture Collection (ATCC), 12031 Parklawn Drive, Rockville, Md. on Sep. 29, 1983 and have been granted ATCC deposit numbers 39455, 39459, 39458, 39456 and 39457, respectively. Recombinant plasmids pHAV$_{LB}$ 39, pHAV$_{LB}$ 108, and pHAV$_{LB}$ 93 have been used for DMA sequencing, to confirm regions of overlap, or to prepare insert probes. Hybridization of an insert fragment from pHAV$_{LB}$ 228 (corresponding to the region from 2.4 to 3.0 kb, relative to scale) to DNA from bacterial colonies was used to select pHAV$_L$ 1307, pHAV$_{LB}$ 12, pHAV$_{LB}$ 58, and pHAV$_{LB}$ 153, for further analysis. Other plasmids which support this map include pHAV$_{LB}$ 153 (1.8–2.7 kb), pHAV$_{LB}$ 58 (1.9–4.0 kb), pHAV$_{LB}$ 12 (2.3–3.3 kb), pHAV$_{LB}$ 87 (4.1–5.8 kb), pHAV$_{LB}$ 201 (5.2–6.7 kb), pHAV$_{LB}$ 38 (5.2–6.9 kb), pHAV$_{LB}$ 56 (5.4–7.1 kb), pHAV$_{LB}$ 185

(5.5–7.5 kb), pHAV$_{LB}$ 24 (5.6–7.5 kb), and pHAV$_{LB}$ 122 (5.7–7.5 kb). Restriction sites have also been mapped with Acc I (2.0 kb), Apa I (5.7 and 6.2 kb), Ava I I (3.5 and 6.6 kb), Bst EII (1.2 kb), Hind III (2.2 kb), Hpa I (0.4 kb), Nde I (1.2 kb), Pvu II (0.8, 1.0, 3.0, 5.2, 5.5, and 7.1 kb), Sac I (3.0 kb), and Xba I (0.8 kb). There is also a site for Nde I (2.5 kb) in pHAV$_{LB}$ 12, pHAV$_{LB}$ 58, pHAV$_{LB}$ 153, and pHAV$_L$ 1307 which is not present in pHAV$_{LB}$ 39. There are no sites for Bgl I, Eco RV, Hae II, Kpn, Mlu I, Nae I, Nar I, Nru I, Pvu I, Sac II, Sal I, Stoa I, Sph I, Stu I, and Tth 111 I.

Plasmids $pHAV_{LB}$ 113, $pHAV_L$ 1307. $pHAV_{LB}$ 228, $pHAV_{LB}$ 148, and $pHAV_{LB}$ 207 overlap to generate a map of about 7.4 kb, which represents at least 99% of the genome of HAV. Inserts from other clones (as indicated in FIG. 6) provided confirmation of overlap regions except for that between $pHAV_{LB}$ 228 and $pHAV_{LB}$ 148. Nick translated $pHAV_{LB}$ 228 insert hybridized to the 1.5 kb PSt I fragment of $pHAV_{LB}$ 148. The overlap as drawn is based on the assumption that there is only one Hinc II site, present in both clones, in the area about 4 kb from the 5' terminus of the genome. No other restriction sites in this region were found by digestion with over 30 other enzymes which have 5 and 6 base recognition sites. Heterogeneity in one restriction site (Nde I) was detected in the region about 2.5 kb from the 5' end of the viral RNA.

Extent of RNA sequence not represented in cDNA clones was determined by primer extension of HAV-infected AGMK cytoplasmic RNA. Racaniello, V. R. and Baltimore, D., *Proc. Natl. Aced. Sci. USA* 78:4887–4891 (1981).

A labelled Pst I/Bam HI fragment (0.2 to 0.7 kb in FIG. 6) from $pHAV_{LB}$ 113 was used as a primer for cDNA synthesis. When the template was cytoplasmic RNA from HAV-infected AGMK cells, the primer was extended to give a discrete band. There was no primer extension when RNA from uninfected AGMK cells was used as a template. When a labelled fragment from closer to the 5' end of the genome was used (Nco I at 0.05 kb in FIG. 6 to Nci I at 0.25 kb) as primer for viral RNA template that was purified from HAV-infected marmoset liver, the primer was similarly extended to a discrete length. Assuming that the 5' termini from HAV RNAs of different passage levels are conserved, we calculated that cloned cDNA extended to within 30 bases of the 5' end of the genome.

Partial Sequence of HAV cDNA. Sequence of cloned HAV cDNA was determined by the Method of Maxam and Gilbert. See, Maxam, A. M. & Gilbert, W., *Methods Enzymol.* 65:499–560 (1980) . The sequences presented in FIGS. 7–9 were determined from individual cDNAs. Because the HAV stock used was not cloned virus, variations may exist between cDNAs that reflect variants in the stock.

In FIGS. 7A–7L nucleotide sequence is presented from $pHAV_{LB}$ 113, $pHAV_{LB}$ 39, $pHAV_L$ 1307, and $pHAV_{LB}$58 in the region corresponding to the 5' portion of HAV RNA. Base 1 corresponds to approximately 0.03 kb on the scale in FIG. 6 and base 23 is the cleavage site for Nco I at 0.05 kb. Codons for translation initiation (ATG) are found at bases 713–715 and 719–721 which are followed by open reading frame for the length of the sequence. The beginning of the long open reading frame, about 750 bases from the 5' end of the genome, corresponds to that for poliovirus RNA. See, Racaniello and Baltimore (1981). The sequences surrounding the putative initiation codons correspond to those described as consensus translation initiation sites in eukaryotic sequences by Kozak (*Microbiological Reviews* 47:1, 1983). Base 2792 is the Nco I site at 2.8 kb in FIG. 6. The predicted HAV amino acid sequences for this region have been compared, using computer programs, with the known capsid protein sequences of other piconaviruses (poliovirus, foot and mouth disease virus, and encephalomyocarditis virus) and locally homologous areas have been discovered. These results support the concept that HAV has a genome organization similar to that of the other piconaviruses, with capsid proteins derived from the amino-terminal portion of the genome polyprotein (sequences shown in FIGS. 7A–7L).

The sequence of cloned cDNA from $pHAV_{LB}$ 93 corresponding to 6.0–7.5 kb in FIG. 6 and the 3' end of HAV RNA is presented in FIGS. 8A–8C. The Pst I cleavage site (base 55) is at 6.0 kb in FIG. 6. There is an open reading frame that extends from the beginning of the sequence to a pair of nonsense codons that are separated by six bases (bases 1409–1420). The second nonsense codon is followed by 51 bases that do not contain an open reading frame initiated by ATG, followed by poly(A), presumed to represent the 3' end of the genome. Using computer programs for comparing amino acid sequences as described above, areas homologous to local regions of the poliovirus RNA polymerase (and the corresponding regions of other piconavirus genomes) have been discovered. In all of the sequences presented above, numerous stop codons in the other reading frames preclude a significant translation product.

EXAMPLE 2

Detection of HAV RNA With Labeled HAV cDNA

Source of RNA

RNA was extracted from African green monkey kidney (AGMK) monolayers, either uninfected or infected with HAV as described in Example 1. RNA was also extracted from fecal suspensions from marmosets that had been experimentally infected with the HM175 strain of HAV. RNA was also extracted from serus or fecal suspensions from humans infected with a variety of HAV strains.

RNA Extraction

All solutions were treated with 0.1% diethylpyrocarbonate prior to use. Total cytoplasmic RNA was isolated from uninfected and HAV-infected AGMK cells. See, Maniatis, T. et al. *Molecular Cloning*, Cold Spring Harbor Laboratory, Cold Spring Harbor, N.Y., 1982. Cells were recovered from monolayers treated with trypsin (20 ug/ml) in 20 mM Tris-HCl (pH 7.4), 0.15M NaCl, and 1 mM EDTA by centrifugation at 2000 g for 5 min at 4° C. Cell pellets were resuspended in lysis buffer (10 mM Tris-HCl [pH 8.6], 0.14M NaCl, 1.5 mM $MgCl_2$, 0.5 % NP-40) containing RNasin (1000 units/ml), vortexed, layered over lysis buffer containing 24% sucrose and 1% NP-40, and centrifuged at 10,000 g for 20 min at 4° C. The resulting upper layer was saved, added to an equal volume of 0.2M Tris-HCl (pH 7.5), 25 mM EDTA, 0.3M NaCl, 2% $NaDodSO_4$, proteinase K (200 ug/ml), and incubated at 37° C. for 30 min. The mixture was extracted with phenol and with chloroform/isoamyl alcohol (24:1, vol:vol). RNA was precipitated from the aqueous phase with ethanol and analyzed by ultraviolet spectroscopy. RNA was similarly extracted from serum and fecal specimens, except that the initial cell lysis and centrifugation steps were deleted. RNA samples were adjusted to 250 ug/ml in 1 mM Tris-HCl (pH 7.5), 1 mM NaCl, 0.02 mM EDTA. Some such samples were digested with ribonuclease A (20 ug/ml) for 20 min at room temperature.

Immobilization of RNA on Nitrocellulose Paper

Samples were applied to nitrocellulose paper using the "dot blot" technique. See, Thomas, P. S., *Proc. Natl. Acad. Sci USA* 77:5201–5205(1980). Nitrocellulose paper was wetted in deionized water, saturated with 3M NaCl, 0.3M trisodium citrate; dried under a lamp; and ruled into 1.5 cm squares with a pencil. A series of 10-fold dilutions of RNA preparations (described above) was made. From each, 4 ul was directly applied into the center of a square on the nitrocellulose sheet resulting in rows of RNA "dots" containing from 1 pg to 1 ug of RNA. Alternatively, the aqueous phase from samples to be applied to a "slot blot" apparatus (see Wahl, *Sequences Application Update #371*, Schleider & Schuell inc., Keene, N. H. 1983) were added to three volumes of 6.15M formaldehyde, 1.5M NaCl, 0.15M trisodium citrate. Samples were heated at 65° for 15 min., then applied using suction onto nitrocellulose paper in a filter manifold (Schleider & Schuell Minifold®II). Buffer (1.5M NaCl, 0.15M trisodium citrate, pH 7.0) was used to presoak the nitrocellulose and wash the sample wells. After drying, the nitrocellulose sheet was baked under vacuum at 80° C. for 2 hr and, prior to hybridization, wetted in 0.75M NaCl, 0.075M trisodium citrate, 50 mM sodium phosphate (pH 6.5) and incubated for 12 hr at 42° C. in 50% vol/vol formamide, 0.75M NaCl, 0.075M trisodium citrate, 50 mM sodium phosphate (pH 6.5), 0.2% NaDodSO$_4$, denatured sheared salmon sperm DNA (100 ug/ml), 0.1% each: bovine serum albumin/polyvinylpyrollindone/Ficoll.

Preparation of DNA Probe

Plasmid pHAV$_{LB}$ 228 was digested with Pst I. After electrophoresis in low melting point agarose, the cloned HAV cDNA insert was isolated and, after a second electrophoretic separation, isolated again from low melting point agarose. It was labeled by nick translation with $^{32}$P to 2 to 6×10$^8$ dpm/ug. Other probes from different regions of the HAV genome have been used with similar results.

Hybridization and Autoradiography

Denatured DNA probe (10 ng/ml) was sealed in a plastic bag containing the nitrocellulose sheet with immobilized RNA and 50% vol/vol formamide, 0.75M NaCl, 0.075M trisodium citrate, 50 mM sodium phosphate (pH 6.5), 0.2% NaDodSO$_4$, denatured sheared salmon sperm DNA (100 ug/ml), 0.04% each: bovine serum albumin/polyvinylpyrollidone/Ficoll for 36 hr at 42° C.

Unbound DNA probe was removed from the nitrocellulose paper by successive washes in 15 mM NaCl, 1.5 mM trisodium citrate, 0.1% NaDodSO$_4$ for 15 min at 50° C. until samples of wash buffer assayed in a liquid scintillation counter indicated that no further removal of probe was taking place. X-ray film was exposed to the nitrocellulose paper with an intensifying screen at −70° C. for varying periods. When RNA from tissue culture was assayed, maximum sensitivity and specificity were obtained using a 17 hr exposure, when only samples from HAV-infected cells indicated binding of probe. No probe bound to those RNA samples that were treated with ribonuclease. In one series of dilutions of RNA from HAV-infected cells, probe binding was detectable with as little as 1 ng total cytoplasmic RNA. Since HAV RNA probably represents less than 1% of the total cytoplasmic RNA in an infected cell, approximately 10$^6$ molecules were detected in this experiment. Results from marmoset and human samples of feces and serum showed that HAV RNA was detected with greater sensitivity than the detection of HAV by immune electron microscopy or by radioimmunoassay. HAV RNA was detected to the level of approximately 1,000 chimpanzee infectious units from a variety of HAV strains.

EXAMPLE 3

Preparation of Chimeric Constructs

Preparation of cDNA clones

Plasmid stocks of cDNA clones of wildtype HAV, the CC variant pHAV/7, and certain chimeras were purified from *Escherichia coli* transformed with the cDNAs constructed by Cohen et al (Cohen et al J. Virol. 63:5364 (1989) and Cohen et al J. Virol. 01:3035 (1987)). Additional chimetic genomes were constructed by ligation of the appropriate restriction digest fragments purified from low-melting-point agarose gels. The AvrII-EcoRI plasmid (FIG. 9) contained all wild-type sequence, except that positions 3889 and 3919 in 2B and positions 4043, 4087, 4222, and 4563 in 2C contained the CC mutations. Position 4185 (Cohen et al J. Virol. 61:50 (1987)) was an A in both the CC and wild-type clones used. The Sac-EcoRI plasmid contained the CC base at positions 3025 in VP1 and 3196 in 2A (Cohen et al Proc. Natl. Acad. Sci. USA 84:2497 (1987)) in addition to those listed above in 2B and 2C. The 5' noncoding region contained either the entire 5' noncoding region of the wild type or all seven mutations identified in the CC clone (Cohen et al Proc. Natl. Acad. Sci. USA 84:2497 (1987)).

In vitro transcription

Transcription was performed as reported previously (Cohen et al J. Virol. 01:3035 (1987)) with slight modifications. After linearization of the plasmid with HaeII, the phenol extraction step was omitted and the DNA was directly precipitated with ethanol. Twenty-four units of Sp6 polymerass (Promega Biotec, Madison, Wis.) was used to transcribe 10 µg of DNA per 100 µl reaction. DNase treatment and RNA purification steps were omitted. The unfractionated transcription mixture was used immediately for transfections or was stored at −80° C.

Synthesis of labeled, genome-length, negative-strand RNA for use in slot-blot analyses was done in a 100 µl reaction mixture prepared as described above, except that the CTP concentration was reduced to 12 µM, 250 µCi of [α-$^{32}$P]CTP (Amersham; >800 Ci/mmol) was added, and 5 µg of plasmid linearized with NarI was transcribed by using 250 U of T7 polymerase (Life Technologies, Grand Island, N.Y.). Unincorporated nucleotides were removed by chromagraphy through a 1-ml G50 Sephadex spin column equilibrated with NETS (100 mM EDTA, 10 mM Tris-HCl, pH 8.0, 0.1% sodium dodecyl sulfate). The column was washed with 50 or 100 µl of NETS, and the eldted RNA was stored at −20° C.

Transfection Assays

Transfectious were performed with T25 flasks containing cell monolayers at approximately 80% confluence. Monolayers were washed three times with 5 ml of Dulbecco modified Eagle medium (DMEM). After aspiration of the medium, the cell monolayers were incubated at room temperature with 0.55 ml of transfection mixture, which was prepared by mixing 50 µl of transcription mixture with 0.25 ml of cold HBSS buffer (21 mM N-2-hydroxyethypiperazine-N'-2-ethanesulfonic acid, 137 mM NaCl, 5 mM KCl, 0.7 mM Na$_2$PO$_4$, 6 mM dextrose [pH 7.05 to 7.2] followed by 0.25 ml of cold MBSS buffer containing 1 mg of DEAE-dextran per ml. After 30 min, 2 ml of DMEM-10% (DMEM supplemented with 10% fetal calf serum, nonessential amino acids, glutamine, 50 µg of gentamicin sulfate per ml, and 2.5 µg of amphotericin B [Fungizone] per ml) was added, and incubation was continued at 34.5° C. for 2.5 h. The medium was removed, cell monolayers were washed once with 5 ml of DMEM, and 5 ml of DMEM-10% was added. Flasks were sealed tightly and incubated at 34.5° C. Long-term cell cultures were maintained in identical medium but with the serum concentration reduced to 2%. Transfection were monitored by immunofluorescence as reported elsewhere (Mathiesen et al Infect. Immun. 18:524 (1977)), except that the first staining with fluorescein-labeled hyperimmune chimpanzee antibodies was followed by a second staining with fluorescein-labeled goat anti-human immunoglobulin G (IgG) antibodies (Kirkegaard and Perry Laboratory, Gaithersburg, Md.). Antibody-stained coverslips were examined by fluorescence microscopy, and the number of cells containing viral antigen was estimated.

Infected cells were harvested by trypsinization of monolayers and stored at −80° C. in DMEM-10%. Viruses were released by three cycles of freeze-thawing of the infected cells.

Slot blot analyses of infected cells

Viruses were harvested from transfected cells after the majority of the cells were infected and then were quantified by slot blot assays using the $^{32}$P-labeled negative-strand RNA (Ticehurst et al J. Clin. Microbiol. 25:1822 (1987)). Samples were adjusted to the same virus genome concentration by dilution with DMEM-10% and were used to inoculate new cells. For growth curves, equal numbers of trypsinized FRhK-4 or CV-1 cells were suspended in 0.5 ml of DMEM-10%, 0.1 ml of virus suspension was added, and the mixture was incubated at 34.5° C. for 1 h. Eight milliliters of DMEM-10% was then added, and 1-ml portions were dispensed to wells of a 24-well tissue culture plate. The following day, the medium was removed and replaced with fresh medium. For titration studies, a 0.2 ml-inoculum of serially diluted virus in DMEM-10% was added to drained, confluent monolayers of CV-1 or FRhK-4 cells in 24-well plates. After 1 h at 34.5° C., 1 ml of DMEM-10% was added and incubation at 34.5° C. was continued.

Figure 10:
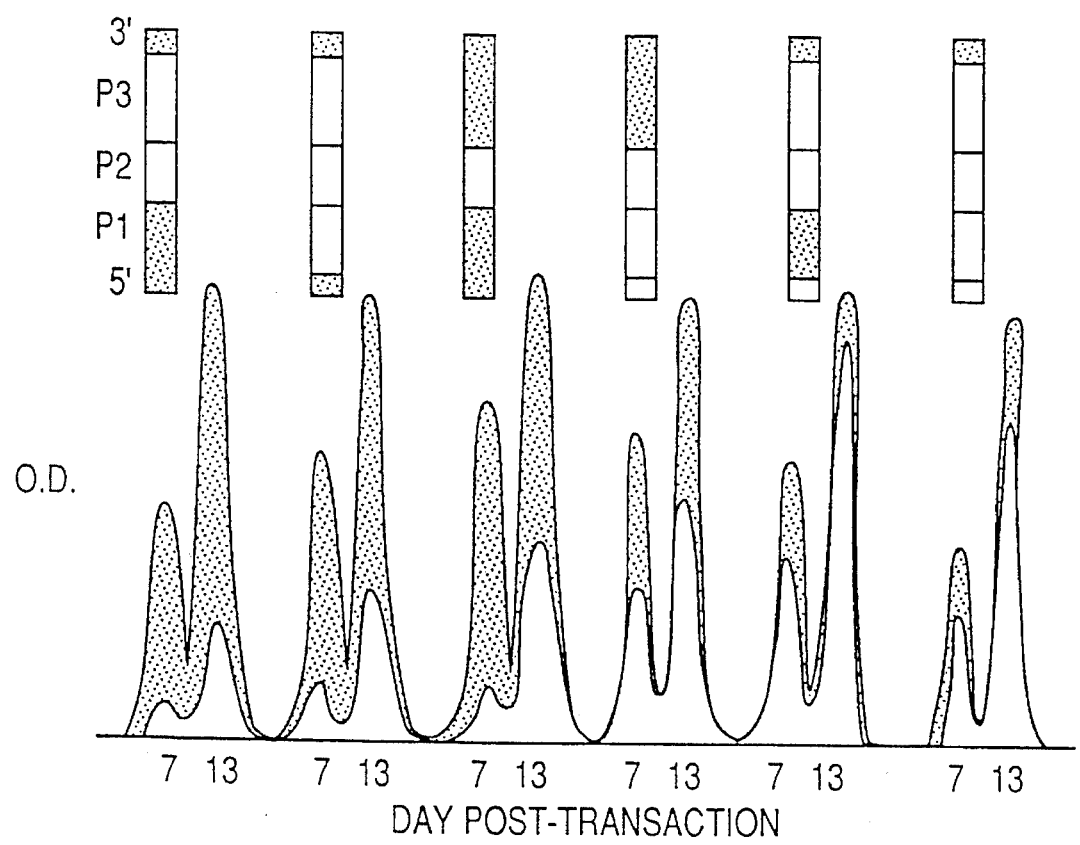
FIG. 10. Differential growth of HAV chimeric viruses in FRhK-4 and CV-1 cells. Parallel cultures of cells were infected with equal amounts of chimeric viruses of the indicated genotype (shaded bar, wild-type genome; open bar, CC genome). Cell lysates were prepared 7 and 13 days postinfection, and vital genomic RNA was quantified by slot blot assays and autoradiography. After densitometry, the tracings were normalized and superimposed for comparison. White curves below each genotype represent replication of virus in CV-1 cells, and shaded curves represent replication in FRhK-4 cells. O.D., optical density.

Samples were taken at the indicated times by adding 1 ml of 2x-concentrated proteinase K buffer (0.02M Tris-HCl, pH 7.8, 0.01M EDTA, 1% sodium dodecyl sulfate) directly to the medium in each well. The resultant culture lysate was stored at −80° C. Eight microliters of lysate was digested with proteinase K, extracted once with phenol, and blotted onto nitrocellulose and processed basically as described previous (Ticehurst et al J. Clin. Microbiol. 25:1822 (1987)), except that the labeled probe was full-length negative-strand RNA. Hybridization was done at 42° C. for 16 h and was followed by a wash at 54° C. Densitometry of radioautographs was performed using a Bio-Rad model 620 video densitometer. To normalize the densitometer curves for comparison in FIG. 10, the highest peak was given an optical density value of 1 and the remaining three peaks were adjusted proportionally by using a BioRad 1-D Analyst software package.

Mutagepesis

The deleted G corresponding to position 4407 was reinserted into the wild-type genome by using the Amersham mutagensis system as directed by the manufacturer (Amersham Corp., Arlington Heights, Ill.). A 25-base-long mutagenic oligonucleotide corresponding to the plus-strand wild-type sequence was synthesized with the reinserred G residue at position 12. Once a correct clone was identified by sequencing, the SacI-EcoRI fragment spanning the 2BC region of the genome was excised and used to replace the corresponding fragment in the wild-type cDNA clone prepared by Cohen et al (Cohen et al J. Virol 63:5364 (1989)).

Growth of HAV/7 in Diverse Cell Lines

Since the basis for the ability to grow in cell culture was unknown, it was of interest to determine whether adaptation to growth in primary cultures of AGMK cells conferred a broad ability to grow efficiently in vitro or whether accelerated growth was restricted to the cell type used in the selection of the adapted variant. RNA transcribed from the pHAV/7 cDNA clone was assayed for infectivity in four different established cell lines. Two of the cell lines were derived from AGMK but appeared to differ in cell origin, since one (BS-C-1) had an epitheliumlike morphology, whereas the other (CV-1) appeared to be fibroblastlike. The third cell line (FRhK-4) was derived from fetal rhesus kidney cells, and the fourth (A549) was derived from human lung. The virus RNA was able to initiate a productive infection in each of the four cell lines, and by day 21 postransfection more than 80% of the cells in each culture were infected. Since the mutations which occurred during adaptation to growth in the primary AGMK cells also conferred the ability to grow efficiently in cells as diverse as those from other primate species, it was of interest to determine which viral functions were involved and whether growth in different cell types was equivalent.

Infectivity of a Wild-Type cDNA Clone

Cohen et al had previously reported that chimeric HAV cDNA clones were infectious for primary AGMK cells provided that the P2/P3 region was from the CC strain (Cohen et al, 1989 J. Virol 63:5364 (1989)). Chimetic constructs containing P2/P3 region from the wild-type cDNA clone were not infectious, suggesting that mutations in this region were important for adaptation to cell culture. However, an alternative explanation was that there was a lethal mutation in the P2/P3 region which was removed during construction of the chimeras. Indeed, when this region of the wild-type cDNA clone used by Cohen et al was resequenced, it was discovered that a G residue at position 4407 in the P2 region had been deleted during growth of the full-length cDNA clone in E. coli. This deletion introduced a frameshift mutation which would be lethal to any chimera containing it.

Figure 9:
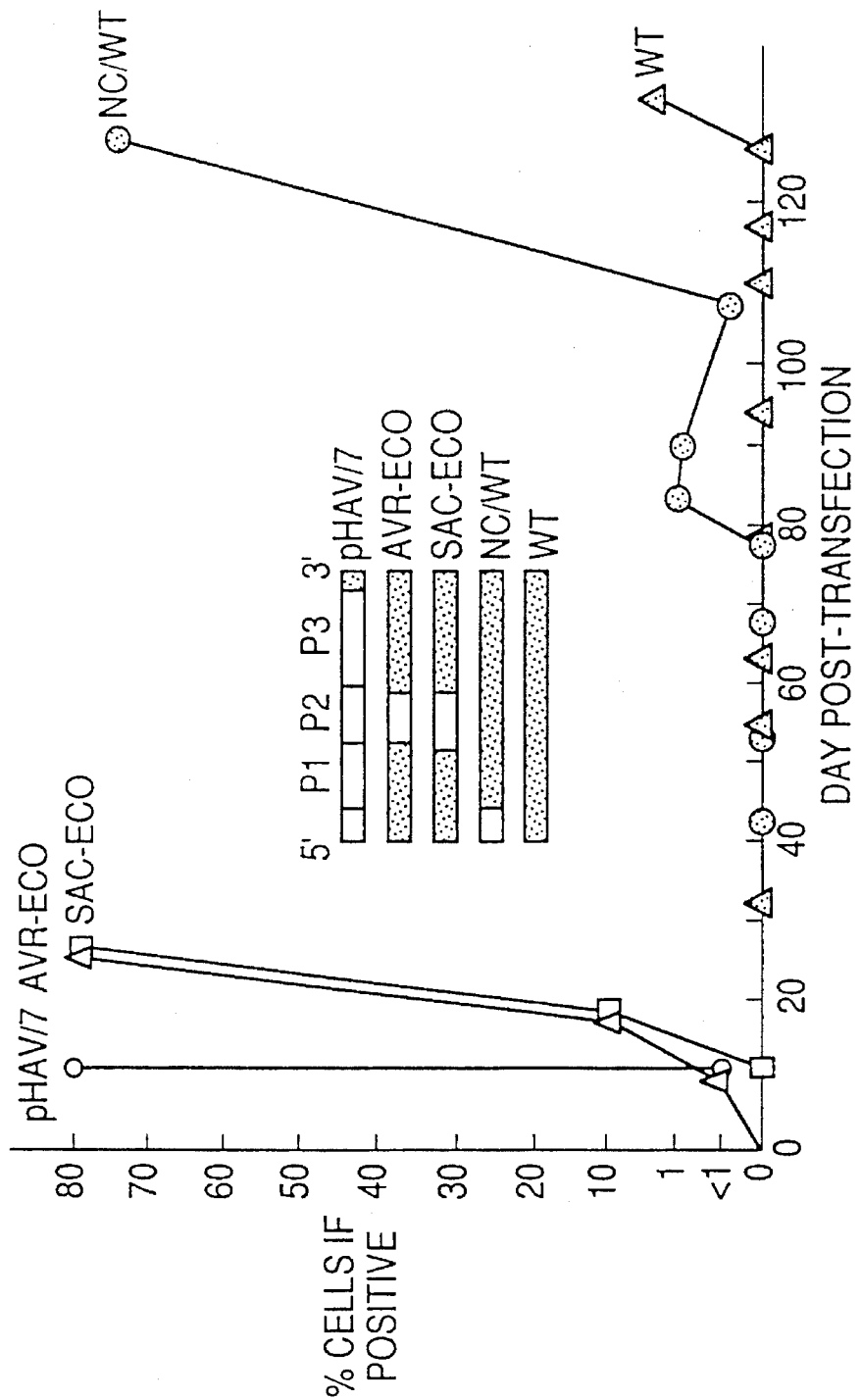
FIG. 9. Transfaction of FRhK-4 cells by HAV genomes containing the P2/P3 region of the wild type (shaded bar) or the cell culture-adapted (CC) variant (open bar). Monolayer cultures of cells were transfected by the DEAE-dextran method, and the number of infected cells was determined by immunofluorescence microscopy.

In order to determine whether the P2/P3 region in fact contained determinants of adaptation, it was necessary to demonstrate that a genome containing this region from the wild-type clone was infections. Therefore, the deleted base was reinserted into the wild-type cDNA clone by oligonucleotide-directed mutagenesis, and four isolates of the corrected clone and a chimeric clone containing the 5' noncoding mutations were tested for infectivity by transfection of FRhK-4 or primary AGMK cells. Cultures of primary AGMK cells transfected with the control CC clone were highly positive after 36 days, with virtually all cells infected. In contrast, virus was not detected up to day 94 in AGMK cultures transfected with the four fully wild-type genomes or the derivative 5' noncoding chimera. The AGMK cultures deteriorated at this time and had to be discarded. However, the 5' noncoding chimera and one of the fully wild-type clones were infectious for the FRhK-4 cells, and in both cases the viruses produced displayed the in vitro growth phenotype of wild-type virus (FIG. 9). Virus was first detected on day 83 in FRhK-4 cell cultures transfected with the chimeric genome which contained all wild-type sequence except for the 5' noncoding region. Spread of this 5' noncoding chimeric virus throughout the culture was very slow; it took 44 days from the time the virus was first detected until more than 75% of the cells were positive in immunofluorescence assays. One fully wild-type clone was not infectious in this experiment, although the clone was viable since it was infectious when tested on a different cell line. Two of the remaining wild-type clones had not produced detectable virus by day 132, when the experiment was terminated. Cells transfected with the fourth wild-type clone (FIG. 9) were negative for HAV on day 117, but approximately 5% of the cells were strongly positive by immunofluorescence assays on day 132. Slot blot analysis of this culture at day 132 confirmed the presence of HAV genomic RNA. Although it proved very difficult to transfect cells containing the P2/P3 region from wild-type HAV, the demonstration that at least three such constructs were viable and produced virus that grew inefficiently in cell culture indicated that some of those mutations which occurred in the P2/P3 region during adaptation to growth in cell culture must indeed be required for accelerated growth.

Mutations in the P2 Region Determine Adaptation

In order to determine which of the mutations in the P2/P3 region led to adaptation, additional chimeras were constructed and tested for infectivity (FIG. 9). Two different constructs containing the P2 region of the CC variant and the P3 region of the wild type grew efficiently in cell culture. Each of two clones containing the AvrII-EcoRI insert and each of five clones containing the Sac-EcoRI insert were infectious, and all produced virus before 3 weeks. Therefore, some or all of the six mutations in the P2 region are sufficient for establishment of infection and accelerated growth in cell culture, and those mutations in the P3 region are not required. In the converse experiment, the P2 region of the CC variant was replaced with that of the wild type, and two clones were isolated. FRhK cells transfected with RNA from these clones had not produced detectable virus by day 70, confirming that mutations in the P2 region are necessary for efficient growth in vitro.

Differential Growth of Chimeras in CV-1 Cells Versus in FRhK-4 Cells

The transfection experiments demonstrated that mutations in the P2 region were critical for adaptation to cell culture, but they did not indicate whether other regions of the genome also influenced growth in vitro. Therefore, viruses from chimeric constructs and pHAV/7 were harvested from transfected primary AGMK cells and used to infect established cell lines in order to provide more quantitative comparisons of their growth potentials in cell culture.

Parallel cultures of CV-1 or FRhK-4 cells were infected with similar numbers of virions, and viral replication was quantified by slot blot analyses and densitometry. Although all five chimeric viruses grew in both cell lines, they differed dramatically in their abilities to do so. Therefore, the densitometer tracings were normalized to eliminate virus differences in absolute growth rates and to emphasize differences due to more efficient growth of a virus in one cell type compared within the other. The three viruses shown on the right of FIG. 10 grew relatively well in either cell line, whereas those shown on the left grew much better in the FRhK-4 cells than in the CV-1 cells. A comparison of the genome composition of each virus suggested that all chimeras containing the 5' noncoding region of the CC genome grew relatively better in CV-1 cells than those viruses which contained the equivalent region from the wild-type genome.

The 5' Noncoding Region Affects Growth Rate and Host Range in Vitro

Figure 11:
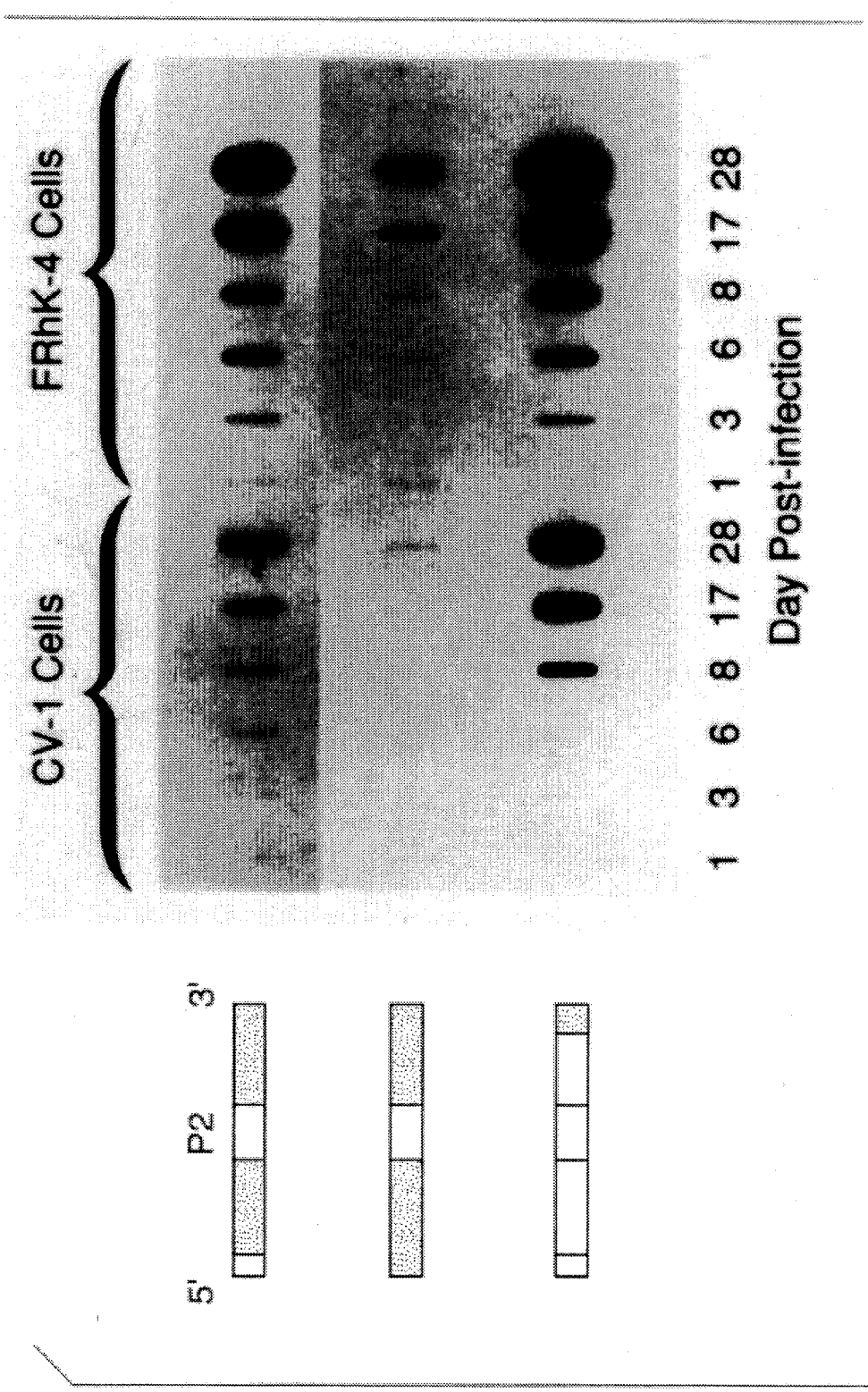
FIG. 11. Growth curves showing effect of 5' noncoding mutations on multiplication of chimeric viruses in FRhK-4 or CV-1 cells. Equal amounts of viruses with the indicated genotypes (shaded bar, wild-type genome; open bar, CC genome) were inoculated onto parallel cultures of the two cell types. Samples were taken on the days indicated, and the amount of viral genomic RNA was quantified by slot blot assays and autoradiography.

A new chimeric virus was constructed to assess directly whether mutations in the 5' noncoding region were responsible for differential growth in the two cell lines. The 5' noncoding region of the CC cDNA clone was substituted for that of a cDNA clone which encoded a virus that grew poorly in CV-1 cells (FIG. 11). RNA transcribed from the new construct and each parent cDNA clone was used to transfect cultured cells. RNA from all three cDNA clones produced virus when transfected into primary AGMK cells or FRhK-4 cells. The two RNAs containing the 5' noncoding region of the CC variant consistently produced virus after transfection of CV-1 cells; in contrast, no virus was detected after eight attempts to transfect CV-1 cells with the RNA containing the 5' noncoding region of the wild-type virus.

In order to assess the effect of the 5' noncoding region in a quantitative way, virus harvested from transfected cells was used to infect cultured cells for either kinetic analyses or titration curves. For the kinetic analyses, equivalent amounts of each virus harvested from transfected primary AGMK cell cultures were inoculated into parallel cultures of CV-1 or FRhK-4 cells. Serial samples were collected, and cumulative virus replication was determined by slot blot assays (FIG. 11). Both the CC virus and the new virus containing the 5' noncoding region of the CC virus grew well and to a similar extent in both CV-1 and FRhK-4 cells. In contrast, the virus which contained the 5' noncoding region from the wild-type clone grew relatively poorly compared with the CC virus; significant replication was detected in the FRhK-4 cell line only after 17 days in culture, and replication was barely detectable in the CV-1 cell line even after 28 days.

Figure 12C:
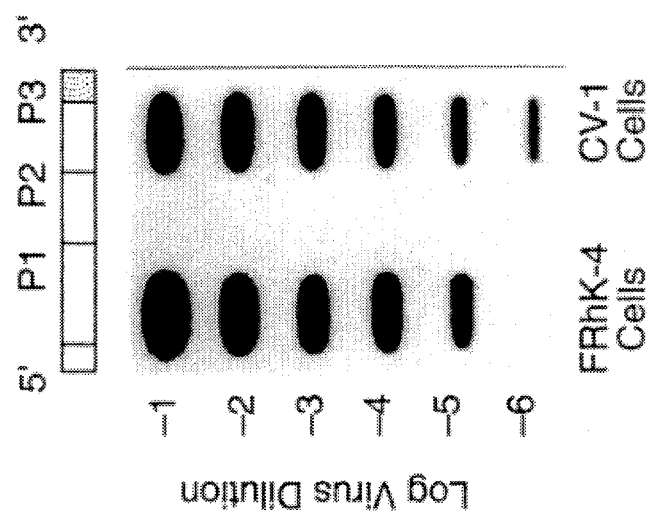
FIGS. 12A–12C present Titration curves showing effect of 5' noncoding mutations on the growth of chimeric viruses in FRhK-4 or CV-1 cells. Serial 10-fold dilutions of each virus indicated (see legend FIG. 11) were inoculated onto parallel cultures of FRhK-4 or CV-1 cells. All samples were harvested on days 20 postransfection and assayed by slot blot assays and autoradiography.
Figure 12B:
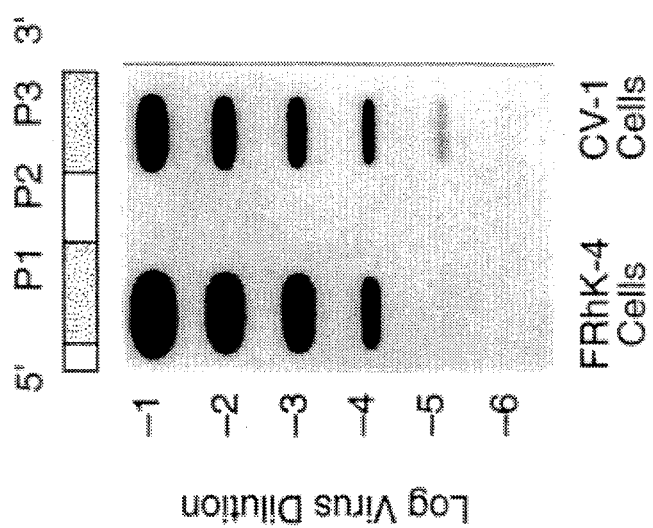
Figure 12A:
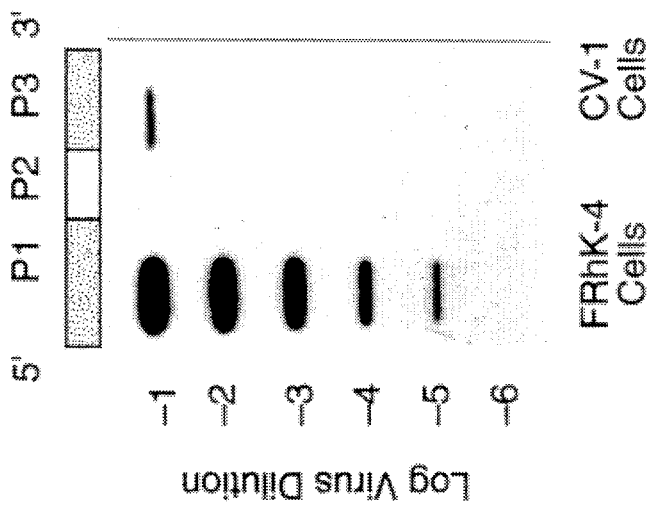

When viruses harvested from transfected FRhK-4 cells were titrated on the two cells lines, growth patterns similar to those of viruses harvested from AGMK cells were observed (FIGS. 12A–12C). Once again, the CC virus and the chimera containing the CC 5' noncoding sequence grew to comparable extents. In both cases, when the 5' noncoding region was from the CC variant, the endpoints of the titration series in the two different cell lines differed at most by 1 log/dilution. On the other hand, the chimera containing the 5' noncoding region from wild-type virus displayed a titration endpoint in CV-1 cells that was 3 to 4 logs lower than that in FRhK-4 cells.

Cell Deposits

The following cell strains containing plasmids designated pHAV, have been deposited at The American Type Culture Collection, Rockville, Md.:

| Strain | pHAV | ATCC Number |
| --- | --- | --- |
| LB58 | LB58 | 39454 |
| LB113 | LB113 | 39455 |
| LB148 | LB148 | 39456 |
| LB207 | LB207 | 39457 |
| LB228 | LB228 | 39458 |
| L1307 | L1307 | 39459. |

Industrial Applicability

The invention described herein is useful in the production of HAV cDNA by recombinant DNA techniques. HAV cDNA is in turn useful in assays for the detection of HAV, in the production of viral antigens, and in the production of antibodies against such antigens.

The entire contents of all applications and references cited above are incorporated herein by reference.

While the present invention has been described in some detail for purposes of clarity and understanding, one skilled in the art will appreciate that various changes in form and detail can be made without departing from the true scope of the invention.

We claim:

1. An assay for the detection of hepatitis A virus in an RNA sample, said assay comprising:
   a. incubating said RNA sample with a labeled hepatitis A virus cDNA sequence under conditions which permit specific hybridization of said cDNA to said sample, said cDNA containing a sequence selected from the group consisting of clones $pHAV_{LB}113$, $pHAV_{LB}1307$, $pHAV_{LB}228$, $pHAV_{LB}148$ and $pHAV_{LB}207$ where said clones.
   b. separating unbound labeled cDNA from said sample; and
   c. detecting any remaining labeled cDNA.

2. The assay of claim 1, wherein said sample is selected from human physiological samples, laboratory animal physiology samples, environmental samples and tissue culture samples.

3. The assay of claim 1, wherein said cDNA is clone $pHAV_{LB}$ 113.

4. The assay of claim 1, wherein said cDNA is clone $pHAV_{LB}$ 1307.

5. The assay of claim 1, wherein said cDNA is clone $pHAV_{LB}$ 228.

6. The assay of claim 1, wherein said cDNA is clone $pHAV_{LB}$ 148.

7. The assay of claim 1, wherein said cDNA is clone $pHAV_{LB}$ 207.

8. An assay for detecting hepatitis A virus comprising a hepatitis A virus cDNA sequence containing a sequence selected from the group consisting of clones $pHAV_{LB}$ 113, $pHAV_{LB}1307$, $pHAV_{LB}228$, $pHAV_{LB}148$ and $pHAV_{LB}207$.

9. The assay of claim 8, wherein said cDNA is clone $pHAV_{LB}$ 113.

10. The assay of claim 8, wherein said cDNA is clone $pHAV_{LB}$ 1307.

11. The assay of claim 8, wherein said cDNA is clone $pHAV_{LB}$ 228.

12. The assay of claim 8, wherein said cDNA is clone $pFLAV_{LB}$ 148.

13. The assay of claim 8, wherein said cDNA is clone $pHAV_{LB}$ 207.

* * * * *